United States Patent
Rofougaran

(10) Patent No.: US 11,435,827 B2
(45) Date of Patent: Sep. 6, 2022

(54) ELECTRONIC TRAINING SYSTEM AND METHOD FOR ELECTRONIC EVALUATION AND FEEDBACK OF SPORTS PERFORMANCE

(71) Applicant: AR & NS INVESTMENT, LLC, Newport Coast, CA (US)

(72) Inventor: Arman Rofougaran, Newport Coast, CA (US)

(73) Assignee: AR & NS INVESTMENT, LLC, Newport Coast, CA (US)

( * ) Notice: Subject to any disclaimer, the term of this patent is extended or adjusted under 35 U.S.C. 154(b) by 488 days.

(21) Appl. No.: 16/557,119

(22) Filed: Aug. 30, 2019

(65) Prior Publication Data
US 2021/0064134 A1   Mar. 4, 2021

(51) Int. Cl.
| | | |
|---|---|---|
| G06F 3/01 | (2006.01) | |
| G06T 19/00 | (2011.01) | |
| A61B 5/11 | (2006.01) | |
| G06N 3/00 | (2006.01) | |
| A63B 69/00 | (2006.01) | |
| G09B 19/00 | (2006.01) | |
| A63B 71/06 | (2006.01) | |

(52) U.S. Cl.
CPC ............ *G06F 3/015* (2013.01); *A61B 5/1118* (2013.01); *A63B 69/00* (2013.01); *A63B 71/0622* (2013.01); *G06N 3/006* (2013.01); *G06T 19/006* (2013.01); *G09B 19/0038* (2013.01)

(58) Field of Classification Search
CPC ....... G06F 3/015; A61B 5/1118; A63B 69/00; A63B 71/0622; G06N 3/006; G06T 19/006; G09B 19/0038
See application file for complete search history.

(56) References Cited

U.S. PATENT DOCUMENTS

| | | | | |
|---|---|---|---|---|
| 2011/0043537 A1* | 2/2011 | Dellon | ..................... | G09B 9/00 345/647 |
| 2011/0251469 A1* | 10/2011 | Varadan | ............... | A61B 5/4806 600/301 |

(Continued)

OTHER PUBLICATIONS

Hamlin et al. ("Monitoring training loads and perceived stress in young elite university athletes." Frontiers in Physiology (Jan. 2019): 34) (Year: 2019).*

*Primary Examiner* — Xin Sheng
(74) *Attorney, Agent, or Firm* — Chip Law Group

(57) ABSTRACT

An electronic training system includes a set of external response sensors and a set of internal response sensors, and control circuitry. The control circuitry is configured to track locomotion and body movements of a user from the set of external response sensors in a sporting event, and electrical brain activity and physiological changes in a body of the user from the set of internal response sensors in a sporting event. Tracked data in the sporting event is annotated as period-of-relevance and period-of-irrelevance. A first sports performance state is assigned to the user for the sporting event based on a combination of a user feedback and sports statistics. The control circuitry outputs a first integrated visual motion model on a display device based on annotated tracked data in the period-of-relevance such that the first sports performance state of the user for the sporting event is discernible by a viewer.

20 Claims, 8 Drawing Sheets

(56) References Cited

U.S. PATENT DOCUMENTS

2013/0060097 A1\* 3/2013 Rubin ..................... A61B 5/11
 600/301
2014/0316230 A1\* 10/2014 Denison ................ A61B 5/168
 600/545

\* cited by examiner

ELECTRONIC TRAINING SYSTEM AND METHOD FOR ELECTRONIC EVALUATION AND FEEDBACK OF SPORTS PERFORMANCE

FIELD OF TECHNOLOGY

Certain embodiments of the disclosure relate to sports performance monitoring systems and technologies. More specifically, certain embodiments of the disclosure relate to an electronic training system and method for electronic evaluation and feedback of sports performance of a user (e.g. a sportsman).

BACKGROUND

Sports have been a meaningful and an integral part of society. With greater attention on sports comes greater attention on improving sports performance of a given sportsman. Now-a-days, a person intending to prepare for a rewarding sporting career start early in life and specialize in particular areas and train year-round to improve their skills. Coaching plays a major role in improving individual and team performance that requires the coach to possess an ability to make quick decisions, supported by an intensive activity of reflection, decision and guidance to influence sporting performance. Typically, human observation and judgment are often prone to biases and it is challenging for even highly skilled coaches to measure small differences in motion and other factors of the given sportsman in a sporting event, which adversely affects next phase of training and sporting performance of the given sportsman. Currently, there exists many heath and performance monitoring systems that monitor and provide recommendations to a player. However, the monitoring and recommendations of the conventional systems are focused to a particular arena of a given sportsman and are often disconnected and not in synchronization with training methodologies of a coach of the given sportsman. Thus, a sportsman is usually in a dilemma regarding which recommendation to follow, what information to implement, and what other to ignore. The biggest challenges faced is information overload from such conventional systems, which is confusing rather than guiding to attain a desired performance. In light of the foregoing, there exists a need for a technical solution that solves the above-mentioned problems and enables comprehensive electronic evaluation and convenient feedback of sports performance.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY OF THE DISCLOSURE

An electronic training system and method for electronic evaluation and feedback of sports performance, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION OF THE DISCLOSURE

Certain embodiments of the disclosure may be found in an electronic training system and method for electronic evaluation and feedback of sports performance. Typically, in conventional systems, the biggest challenges faced is information overload. As a result of the information overload, a sportsman is usually in a dilemma with regards to which recommendation to follow, what information to implement, and what other to ignore, which is very confusing rather than guiding to attain a desired sports performance.

The electronic training system provides an integrated solution that integrates a user feedback, for example, feedback from a professional coach into technological evaluation of sports performance to be able to achieve a comprehensive and an accurate evaluation of sports performance of a user. The output from the electronic training system is user-friendly and is easily discernible by a user. The electronic training system complements and improves the existing training and feedback system by pinpointing the areas to focus in a systematic analysis and feedback of sports performance. Such electronic evaluation and feedback results in improving a current sports performance state of a user and achieving a target sports performance state. The electronic training system is highly receptive to various responses generated in a body of a user due to the provisioning of stimulus and can adjust the stimulus as per the responses generated. Further, the electronic training system is able to provide quantifiable feedback on the progress and performance of the user. The disclosed electronic training system and method may be used specifically for an individual or for a team for electronic evaluation and feedback of sports performance. In the following description, reference is made to the accompanying drawings, which form a part hereof, and in which is shown, by way of illustration, various embodiments of the present disclosure.

Figure 1:
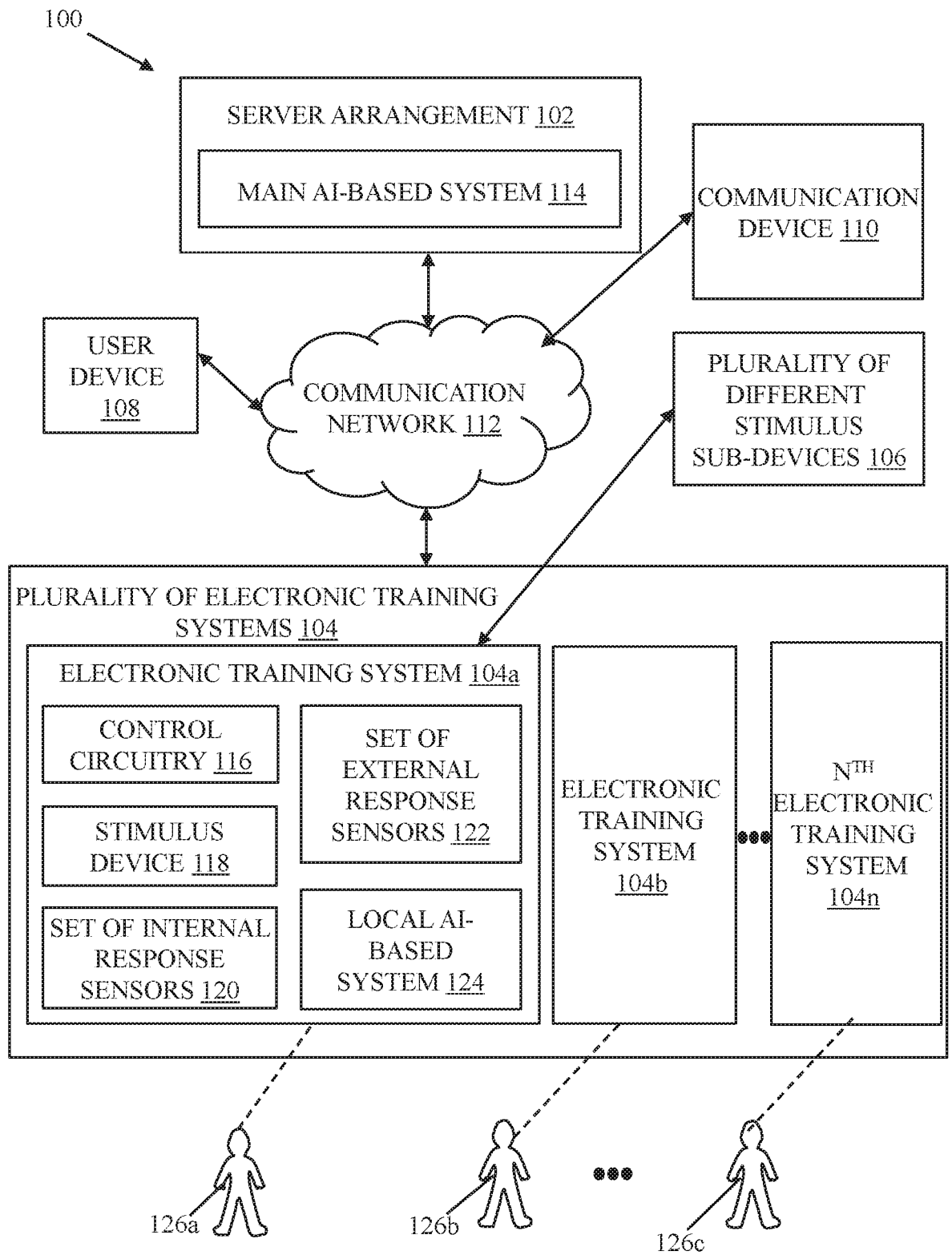
FIG. 1 is a block diagram that illustrates an exemplary environment of an electronic training system for electronic evaluation and feedback of sports performance, in accordance with an exemplary embodiment of the disclosure.

FIG. 1 is a block diagram that illustrates an exemplary environment of an electronic training system for electronic evaluation and feedback of sports performance, in accordance with an exemplary embodiment of the disclosure. With reference to FIG. 1, there is shown an exemplary network environment 100. The network environment 100 includes a server arrangement 102, a plurality of electronic training systems 104, a plurality of different stimulus sub-devices 106, a user device 108, a communication device 110, and a communication network 112.

The server arrangement 102 may include a main Artificial Intelligence (AI)-based system 114. The plurality of electronic training systems 104 may include multiple electronic training systems 104a, 104b, . . . , 104n. The electronic training system 104a may include control circuitry 116, a stimulus device 118, a set of internal response sensors 120, a set of external response sensors 122, and a local AI-based system 124. It will be apparent to those of skill in the art that other electronic training systems 104b, . . . , 104n are functionally similar to the electronic training system 104a. A plurality of users 126a, 126b, . . . , 126n may be associated with the plurality of electronic training systems 104. For example, the user 126a is associated with the electronic training system 104a, the user 126b is associated with the electronic training system 104b, and the user 126n is associated with the electronic training system 104n. Various devices in the network environment of the health maintenance system 100 may be communicatively coupled with each other via the communication network 112.

The server arrangement 102 includes suitable circuitry, interfaces, and/or logic configured to instruct the plurality of electronic training systems 104 to provide a plurality of stimuli on various body portions of the plurality of users 126a, 126b, . . . , 126n. The server arrangement 102 is further configured to instruct the plurality of electronic training systems 104 to sense and measure levels of a plurality of responses generated in the body portions of the plurality of users 126a, 126b, . . . , 126n due to the application of the plurality of stimuli on the body portions of the plurality of users 126a, 126b, . . . , 126n. The server arrangement 102 is further configured to receive primary information pertaining to a plurality of stimulus-response pairs from the plurality of electronic training systems 104, based on the measurement of the plurality of responses. The server arrangement 102 is further configured to receive, from the plurality of electronic training systems 104, supplementary information associated with the plurality of users 126a, 126b, . . . , 126n on which the plurality of stimuli was applied. The server arrangement 102 may be configured to convert the primary information and the supplementary information into an AI-based system-readable data format. Examples of the server arrangement 102 may include, but are not limited to, an application server, a cloud server, a web server, a database server, a mainframe server, or a combination thereof. Further, it should be appreciated that the server arrangement 102 may be a single hardware server or a plurality of hardware servers operating in a parallel or distributed architecture.

For the sake of brevity, operations of each of the plurality of electronic training systems 104 are explained with respect to the electronic training system 104a. The electronic training system 104a includes the local AI-based system 124 that is communicatively coupled to the main AI-based system 114. The electronic training system 104a includes suitable logic, circuitry, and/or interfaces configured to annotate tracked data in a sporting event as a set of period-of-relevance and a set of period-of-irrelevance based on a correlation in the locomotion, body movements, electrical brain activity, and physiological changes tracked for the user 126a in the sporting event. The electronic training system 104a is used for electronic evaluation and feedback of sports performance for the user 126a. In some embodiments, the electronic training system 104a may be configured to receive control instructions, in a connected mode, from the server arrangement 102 for electronic evaluation and to provide feedback of sports performance to the user 126a. In some embodiments, the electronic training system 104a may be configured to provide feedback one or more users, such as the user 126a on its own, in the absence of online connectivity or when a standalone mode is set at the electronic training system 104a.

Figure 2:
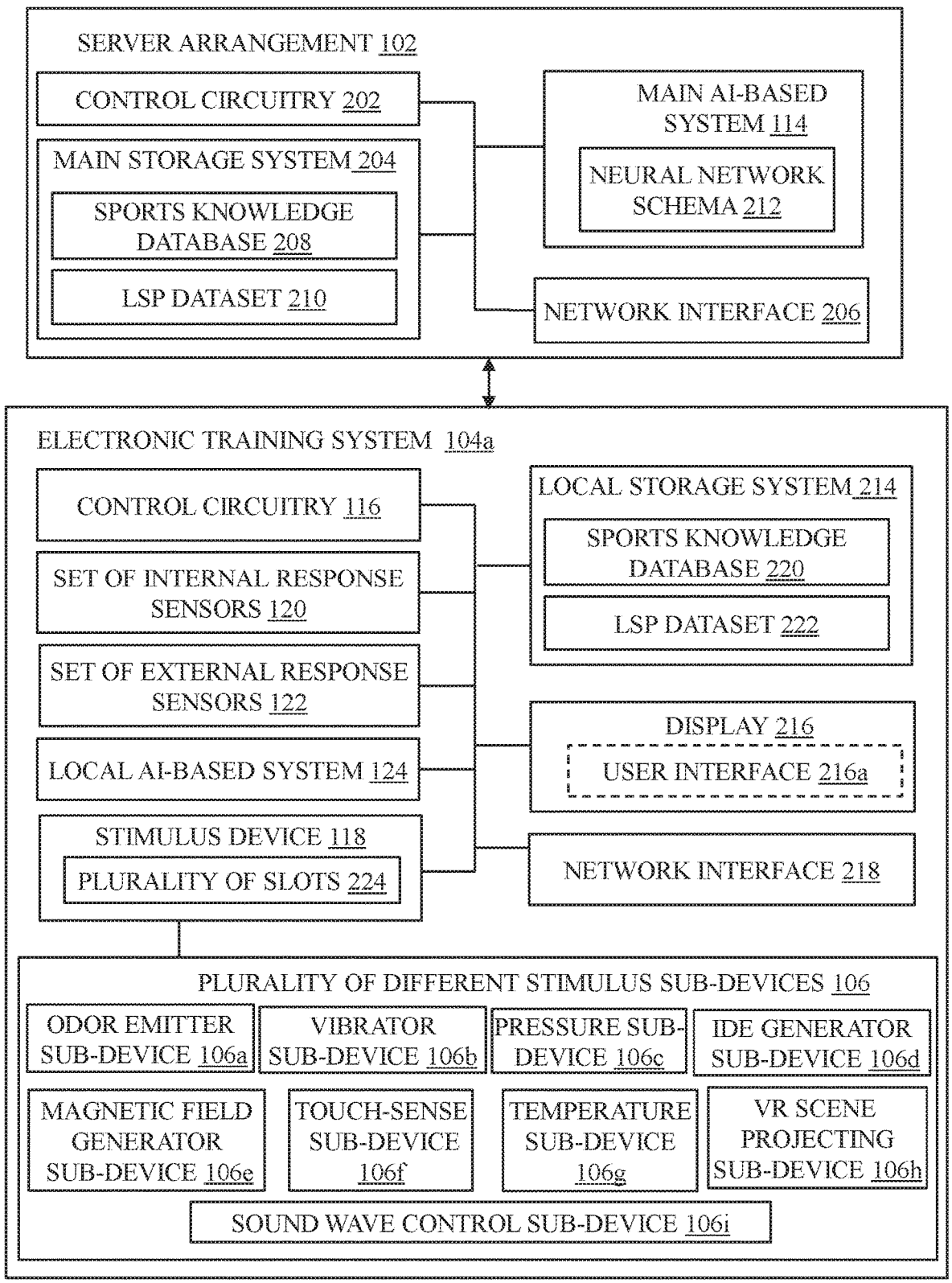
FIG. 2 is a diagram that illustrates different components of a server arrangement and an electronic training system of FIG. 1, in accordance with an exemplary embodiment of the disclosure.

The plurality of different stimulus sub-devices 106 may correspond to modular attachments that may be attached to any of the plurality of electronic training systems 104, for example, the electronic training system 104a, for applying different types of stimuli to the user 126a. Each of the plurality of different stimulus sub-devices 106 may include suitable logic, circuitry, and/or interfaces configured to generate a stimulus such as a pressure stimulus, a temperature-based stimulus, a vibration stimulus, a sound wave stimulus, a virtual reality (VR) stimulus, an odor stimulus, a touch-based stimulus, and a magnetic stimulus. Examples of the plurality of different stimulus sub-devices 106 are shown in FIG. 2.

The user device 108 may be for an individual, institution, or agency that provides sports training or coaching services to a sportsman. For example, a coach, a dietician, an endurance trainer, and the like, may be considered the individual that provides the coaching or sports training. The institution or agency may be a training and coaching center, or a genetic screening laboratory or any entity that provides advisory services to users. In an implementation, the user device 108 may be associated with a coach. Examples of the user device 108 may include, but is not limited to a smartphone, a human machine interface (HMI), a handheld device, a consumer electronic device, and other computing device. In some embodiments, the user device 108 may be a part of a machine, for example, a medical equipment.

The communication device 110 may correspond to a telecommunication hardware (e.g. a relay node or a repeater device). Examples of the communication device 110 may include, but are not limited to a 5G-capable repeater device, an Evolved-universal terrestrial radio access-New radio Dual Connectivity (EN-DC) device, a New Radio (NR)-enabled device, or a mmWave-enabled telecommunication device. The communication device 110 may facilitate communication in both sub 30 gigahertz to above 30 gigahertz. In one example, the communication device 110 may receive/transmit the RF signals from/to a base station or from another network node.

The communication network 112 may include a medium through which the various devices in the network environment, such as the server arrangement 102, the plurality of electronic training systems 104, the user device 108, the communication device 110, and the user device 108, may communicate with each other. In some embodiments, a secured and dedicated communication channel may be established between the plurality of electronic training systems 104 and the server arrangement 102. The communication network 112 may be implemented by use of various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), ZigBee, EDGE, IEEE 802.11, light fidelity (Li-Fi), 802.16, IEEE 802.11s, IEEE 802.11g, multi-hop communication, wireless access point (AP), device to device communication, cellular communication protocols, or Bluetooth (BT) communication protocols, or a combination thereof. Other examples of the communication network 112 may include, but are not limited to, the Internet, a cloud network, a Long Term Evolution (LTE) network, a secured Wireless Local Area Network (WLAN), a Local Area Network (LAN), a telephone line (POTS), or other wired or wireless network.

The main AI-based system 114 includes suitable circuitry, interfaces, and/or logic configured to train one or more neural network models, for example, recurrent neural network (RNN), such as Long Short Term Memory networks (LSTM) networks, convolution neural network (CNN), deep neural network (DNN), or an artificial neural network that may be a combination of the RNN and CNN networks. For example, the main AI-based system 114 may train the one or more neural network models to find a relationship between the plurality of stimuli and the plurality of responses generated in the body portions of the users 126a, 126b, . . . , 126n. In accordance with an embodiment, the trained model(s) is then deployed in one or more components of each of the plurality of electronic training systems 104, for example, the local AI-based system 124. The deployed pre-trained neural network model(s) is remotely updatable as and when required. In some embodiments, the server arrangement 102 may establish a dedicated and secured link, via the communication network 112 or by use of the communication device 110 (e.g. a 5G enabled repeater device) to update various programmable components, such as the deployed pre-trained neural network model, of the plurality of electronic training systems 104. In an embodiment, the main AI-based system 114 may employ supervised or unsupervised learning model. The main AI-based system 114 may employ machine learning algorithms, such as supervised, unsupervised, semi-supervised, or reinforcement machine learning algorithms for operation thereof. Typically, the machine learning algorithms refer to a category of algorithms employed by a system that allows the system to become more accurate in predicting outcomes and/or performing tasks, without being explicitly programmed.

The control circuitry 116 comprises suitable logic, circuitry, and interfaces configured to process sensor data acquired from the set of internal response sensors 120 and the set of external response sensors 122. Examples of the control circuitry 116 include an Application-Specific Integrated Circuit (ASIC) processor, a Complex Instruction Set Computing (CISC) processor, a combination of a central processing unit (CPU) and a graphics processing unit (GPU), a microcontroller, and/or other hardware processors.

The stimulus device 118 may correspond to a human senses' stimulator device. The stimulus device 118 may comprise suitable logic, circuitry, and/or interfaces configured to applying the plurality of stimuli to the body portions of the user 126a to increase sports performance. Examples of the plurality of stimuli may include, but are not limited to, calibrated pressure, calibrated vibration input, calibrated electric input, sound waves, magnetic input, a virtual reality or mixed reality environment output, and a combination of physical therapy and virtual reality output. The stimulus device 118 may operate under the control of the control circuitry 116. In accordance with an embodiment, the stimulus device 118 may include various stimulus sub-devices for providing different types of stimuli to different body portions of a user. In accordance with another embodiment, the stimulus device 118 may include a plurality of slots (as shown in FIG. 2) to detachably attach the plurality of different stimulus sub-devices 106 in the plurality of slots in a modular arrangement.

The set of internal response sensors 120 includes suitable logic, circuitry, and/or interfaces configured to sense and measure a level of an internal response generated within a body of a user. In accordance with an embodiment, the set of internal response sensors 120 may be attached to or placed on a body of a user (such as the user 126a) in a non-invasive manner when the user is undergoing training for a sporting event or involved in actual sports activities in the sporting event. Examples of the internal responses that may be sensed and measured by the set of internal response sensors 120 may include, but are not limited to, electrical brain activity and physiological changes in a body of a user. In one example, the set of internal response sensors 120 may comprise an electromyograph for sensing and measuring activity in muscles and nerves. The set of internal response sensors 120 may further include a blood pressure monitor, a heart rate monitor, a pulse rate monitor, a temperature sensor, a low power magnetic resonance imaging system, and/or the like. The set of internal response sensors 120 may operate under the control of the control circuitry 116.

The set of external response sensors 122 includes suitable logic, circuitry, and/or interfaces configured to sense and measure an external change discernible from external surface of the body of a user. Examples of the external response that may be sensed and measured by the set of external response sensors 122 may include, but are not limited to, locomotion (i.e. movement of individual from one place to another), body movements (e.g. movement of joints, limbs, and specific sections of the body), facial expressions, skin colour, a body posture, gestures, and/or voice feedback. In one example, the set of external response sensors 122 may include an imaging device, a light detection and ranging (LiDAR) sensor, and/or a radio detection and ranging (RADAR) sensor for sensing changes in facial expressions and gestures of the user when stimulus is provided to the user. The set of external response sensors 122 may further include an audio sensor for sensing the voice feedback of the user when the stimulus is provided to the user. The set of external response sensors 122 may operate under the control of the control circuitry 116.

In operation, there may be a training phase and an operational phase of the electronic training system 104a. In the training phase, the control circuitry 116 of the electronic training system 104a may be configured to track movements of each body part of a plurality of body parts of the user 126a in relation to a corresponding reference point. The tracking may occur in a plurality of sporting events from a combination of the set of external response sensors 122 and the set of internal response sensors 120. The reference point for a specific body part may be selected based on a current position of the specific body part that is tracked. In a training phase, depending on the type of a sporting event, a movement dataset from a plurality of movements dataset is retrieved and set as default to be used for reference. For example, if a golf match is played, accordingly a movement dataset prespecified for golf is retrieved. The movement dataset has collection of poor to best shots and associated motion coordinates of many test users and known video analysis from other players involved in golf play. The movements of rotate, tilt, way or manner of holding club face, posture, force applied in a stroke, etc. may be used as reference. The plurality of movements dataset may be stored in sports knowledge database (e.g. the sports knowledge database 208 or 220 in FIG. 2). Similarly, for a different sport, such as soccer, locomotion movements, i.e. how a player moves from one position to another position in a field where the sport is played, and the footwork may be more useful than movement of hands. Thus, more emphasis may be provided on legs than on hands tracking. Beneficially, having a specific movement dataset for a specific sport results in removal of artifacts and noise in tracking, and fine details and biomechanics may be captured with less computational processing power as a result of focused approach in tracking specific body portions more precisely.

Additionally, at the time of tracking, different reference points may be dynamically and temporally set for tracking different body parts. For example, a left hand and a right hand of the user 126a may be tracked in relation to a hip joint in a case where the user 126a is upright in normal standing position. However, on bending or in squat position, a reference point in ground (e.g. point of squat) may be dynamically set from tracking hand movements in an example. Torso twist (or rotate) may be tracked from a reference vertical plane (e.g. a coronal plane and a sagittal plane of human anatomy). A bend motion may be tracked from a transverse plane. Further, the control circuitry 116 may be further configured to determine relative motion of one body part from other body parts of the plurality of body parts based on the sensor data acquired form the set of external response sensors 122. Beneficially, the tracking of each body part of the plurality of body parts of the user 126a in relation to a corresponding reference point that is automatically set as per body posture facilitates enhanced tracking and motion data capture.

In accordance with an embodiment, the control circuitry 116 in the training phase may be further configured to track electrical brain activity of the user 126a in the plurality of sporting events by use of the set of internal response sensors 120. Typically, neurons in human brain communicate through electrical impulses. Such communication enables the brain to coordinate behaviour, sensation, and emotion. The electrical impulses signals are measurable using sensors attached to brain. There are usually spontaneous oscillations that defines the electrical activity of the human brain and the variation in these oscillations defines changes of state and type of brain activity. Many individuals for a same action or activity may have same, slightly different, or varied electrical brain activity. Further, same action under different circumstances in a sporting event may result in different electrical brain activity in same or different areas of brain. Thus, tracking electrical brain activity of individual user over a period of time provides a pattern of similarity and variations and when these similarity and variations are tagged with resultant performance, for example, good performance, average, or poor performance over a period of time, such data becomes powerful tool in electronic analysis of sports psychology just before a sporting event, during sporting event, and post specified time interval after completion of the sporting event.

In an example, wearable, whole-scalp electroencephalogram (EEG) and/or functional near-infrared spectroscopy (fNIRS) may be embedded in a headgear, such as a helmet worn by a player, for direct monitoring of brain activity during a sporting event or during training, exercise, and practice for a sporting event. A known technical problem with tracking electrical brain activity, for example, using EEG is that genuine cerebral data is often contaminated by artifacts of non-cerebral origin, for example, various body movement during exercise and when performing sports activities and/or due to physical exertion in a sporting event. The control circuitry 116 effectively handles such tracking of electrical brain activity by masking the effect of such artifacts, to obtain reliable tracked data. The control circuitry 116 is further configured to tag such electrical brain activity with stationery and motion parameters (e.g. "acquired when stationary" and "acquired when in motion"). Beneficially, this provides valuable information of potential artefacts signal patterns associated with wearable devices that are used to capture the electrical brain activity, such as EEG, thereby reduces the risk of misinterpretation during tracking of such electrical brain activity in a given sporting event. Such signal patterns may be removed (or masked or ignored) from the sensor data related to electrical brain activity. For example, comparison of amplitudes in alpha and beta band for various a time interval before, during and after specified time interval of a shot in a sporting event, and associated result of the shot (e.g. good, average, or bad performance) provides through understanding of signals that are associated with good performance, for example, 90% of time.

In accordance with an embodiment, the control circuitry 116 in the training phase may be further configured to track physiological changes induced in the body of the user 126a in the plurality of sporting events by use of the set of internal response sensors 120. The physiological changes in the body of a user may refer to changes in activity in muscles or nerves, blood pressure, heart rate, breathing rate, body temperature, and/or pulse rate. For example, in aerobic training, weight and volume of a heart increases. In another example, myocardium muscle experience hypertrophy (an enlargement). Further, fiber composition in muscles also changes or certain fibers, such as fast-twitch fibers, are more used in quick and short body movements, such as performed in hockey. The capacity of the capacity of VO2 (volume of oxygen) also increases with sports endurance. VO2 refers to the maximum rate of oxygen consumption measured during incremental exercise or sporting activity. Moreover, hormonal, lipid, carbohydrates composition may also change over a period of time. Further, the physiological changes induced in the body may further include amount of lactate and glucose in the body. These variables when tracked in the plurality of sporting event for a same user, such as the user 126a, may be analyzed to provide a detailed understanding of where the user 126a needs to focus to improve sports performance.

In accordance with an embodiment, the control circuitry 116 may be configured to store tracking data obtained from the tracked locomotion, the tracked body movements, the tracked electrical brain activity, and the tracked physiological changes for the user 126a in each sporting event of the plurality of sporting event. The control circuitry 116 may be configured to track and acquire a plurality of variables associated with tracked locomotion, the tracked body movements, the tracked electrical brain activity, and the tracked physiological changes in synchronization with each other. Alternatively stated, individual tracking may not provide reliable and meaningful data, but when tracked in association with other, the artefacts and noise related to different sensors of the set of internal sensors 120 and the set of external sensors 122 are minimized or almost nullified.

In accordance with an embodiment, the control circuitry 116 in the training phase may be further configured to assign a sports performance state to the user 126a at completion of each sporting event of the plurality of sporting events based on a combination of sports statistics acquired from at least one specified online data source and at least one of a coach-feedback of the user 126a or a self-feedback by the user 126a. The electronic training system 104a takes the advantage of an expertise of a coach and incorporates such feedback into the electronic training system 104a for practical and usable output which is more relevant for the user 126a undergoing the sports training as well as the coach providing the sports training to enhance sports performance. Typically, a sportsman is classified into a beginner stage, an intermediate stage, and a professional stage. Each stage may further have different sports performance state, which may be defined as level 1 to level 10, level 1 the lowest performance level of a given stage and the level 10, the highest level. When a sportsman achieves level 10, next stage is automatically assigned, and the counter is reset to level 1. Once the sportsman achieves the level 10 of professional stage, a new stage is created with a difficulty level higher than the previous stage, and the counter of level is reset to level 1. Thus, the sports performance state is a combination of a stage and a level assigned to that stage. The sports performance state not only employs user-feedback (such a coach feedback or a self-feedback of the user 126a, or a combination of the coach feedback and the self-feedback), but also acquires sports statistics of the user 126a from online information source, such as a social network, a sports website, and the like. The sports statistics may be used to determine whether the sports performance feedback from the coach and the self-feedback is not having any human biases, and also a comparative performance of the user 126a in relation to other players of a given sporting event is also checked. Based on the combination of the sports statistics, the coach-feedback, and the self-feedback, a more accurate and unbiased sports performance state may be assigned in each sporting event of the plurality of sporting event by the control circuitry 116 in the training phase.

In accordance with an embodiment, the control circuitry 116 may be configured to store a learned sports performance dataset in the server arrangement 102 or a local storage system. The learned sports performance dataset may include a plurality of historical sports performance states and associated tracked data by the set of internal response sensors 120 and the set of external response sensors 122. The plurality of historical sports performance states corresponds to the assigned sports performance state to the user 126a at completion of each sporting event of the plurality of sporting events. The tracked data for each sporting event is tagged with metadata that facilitates extraction of tracked data for a specific sporting event from the plurality of sporting events.

In accordance with an embodiment, the control circuitry 116 may be further configured to annotate tracked data in the sporting event as a set of period-of-relevance and a set of period-of-irrelevance based on a correlation in the tracked locomotion, the tracked body movements, the tracked electrical brain activity, and the tracked physiological changes for the user 126a in each sporting event of the plurality of events. In an example, the set of period-of-relevance may be determined by segregation of the tracked data for a given sporting event into short action time intervals (i.e. a time interval that defines a specific shot or action in a sporting activity). In an example, the time interval may include an elapsed time period before a shot, during a shot, and a specified time period after the shot in a tennis sport. Such action time intervals may be then correlated with other tracked data related to the tracked electrical brain activity, and the tracked physiological changes for the user 126a. The remaining data where no relevant action is detected from all the tracked body movements, the tracked electrical brain activity, and the tracked physiological changes may be ignored and tagged as the set of period-of-irrelevance. The annotated tracked data as the set of period-of-relevance for each sporting event along with the assigned sports performance state may be used as training dataset for the local-AI based system 124. The learned sports performance dataset further includes the learnings derived from such annotated tracked data as the set of period-of-relevance for each sporting event along with the assigned sports performance state.

In accordance with an embodiment, the plurality of electronic training system 104 may operate in a connected mode or a standalone mode. In the connected mode, each electronic training system 104a, 104b, . . . , 104n, may be configured to communicate the annotated tracked data as the set of period-of-relevance for each sporting event along with the assigned sports performance state to the server arrangement. Thereafter, the server arrangement 102 may be configured to extract datapoints as training dataset from the annotated tracked data that corresponds to the set of period-of-relevance and convert the datapoints into an AI-readable format to feed into the main AI-based system 114. In the standalone mode, the extraction of datapoints as training dataset from the annotated tracked data that corresponds to the set of period-of-relevance and conversion of the datapoints into an AI-readable format occurs at corresponding electronic training system 104a, 104b, . . . , 104n.

Like the training phase, the control circuitry 116 in the operational phase may be further configured to track locomotion and body movements of the user 126a from the set of external response sensors 122 in a sporting event (i.e. a new sporting event). The control circuitry 116 may be further configured to track electrical brain activity and physiological changes in a body of the user 126a from the set of internal response sensors 120 in the sporting event. The control circuitry 116 may be further configured to annotate tracked data in the sporting event as a set of period-of-relevance and a set of period-of-irrelevance based on a correlation in the tracked locomotion, the tracked body movements, the tracked electrical brain activity, and the tracked physiological changes for the user in the sporting event. The control circuitry 116 may be further configured to assign a first sports performance state to the user 126a at completion of the sporting event based on a combination of a user feedback (e.g. a coach feedback or self-feedback of the user 126a) and sports statistics acquired from at least one specified data source (e.g. an online data source).

The control circuitry 116 may be further configured to output a first integrated visual motion model on a display device based on annotated tracked data in the set of period-of-relevance. The integrated visual motion model comprises a first visual representation of the tracked locomotion and the body movements, a second visual representation of the tracked electrical brain activity, and a third visual representation of the tracked physiological changes in the body that are merged in the first integrated visual motion model and time-controlled at output such that the first sports performance state of the user 126a for the sporting event is discernible by a viewer. In accordance with an embodiment, the first integrated visual motion model is a three-dimensional (3D) computer graphic model (hereinafter referred to as 3D model) of the user 126a that reflects the external as well internal changes in a meaningful synchronization during the set of period-of-relevance in the sporting event. For example, in conventional systems when a player playing golf plays a stroke, the motion of arms and body posture may be captured by image-capture devices, and may be viewed later in slow-motion to manually evaluate sports performance with respect to result achieved for that stroke, a ball misses to be holed. However, in conventional systems, many other reasons and causes that lead to the result are usually ignored. In contrast to the conventional systems, the output of the first integrated visual motion model provides a synergistic view of changes in the tracked locomotion and the body movements, the tracked electrical brain activity, and the tracked physiological changes in the body when the player playing golf plays the stroke. In an example, the second visual representation of the tracked electrical brain activity may be visible within the 3D model of the user 126a. similarly, the third visual representation of the tracked physiological changes in the body may be visible within the 3D model of the user 126a. In other words, multiple 3D models (the first, second, and third visual representation) are merged with each other to reflect changes in a synergistic manner. An example of the first integrated visual motion model is shown and described in FIG. 3B.

In accordance with an embodiment, the control circuitry 116 in the operational phase may be further configured to output a second integrated visual motion model along the first integrated visual motion model as feedback. The second integrated visual motion model is outputted based on a comparison of the assigned first sports performance state with the stored learned sports performance dataset that comprises the plurality of historical sports performance states and associated tracked data. The second integrated visual motion model indicates a set of positive performance activities (e.g. good performances) and a set of negative performance activities (e.g. bad performances) in relation to the first sports performance state of the user 126a for the sporting event.

In accordance with an embodiment, the user 126a may want to set a goal to reach a target sports performance by constantly challenging self for improvement in sports performance. The electronic training system 104a provides a mechanism by which a user, such as the user 126a, is challenged to improve not only technical skills in sports, but also phycological and tactical training is imparted using various stimulus provided by the stimulus device 118. The control circuitry 116 may be further configured to receive an input via a user interface rendered on a display device communicatively coupled to the electronic training system 104a. The input comprises a current sports performance state and a target sports performance state of the user 126a. The input may include user formation pertaining to a current sports performance state and a target sports performance state that is intended to be achieved for the user 126a. In an embodiment, other details, for example, physical characteristics of the user 126a, a geography, a feedback from a dietician, a current training plan, may also be provided via the user interface 216a.

In accordance with an embodiment, the control circuitry 116 may be further configured to retrieve at least one priori stimulus from a sports knowledge database based on the received input. In one example, the priori stimulus may correspond to a stimulus that is known based on existing knowledge in sports to influence one or more sports performance factors in the current sports performance state of the user 126a. The control circuitry 116 may be further configured to determine a set of test stimuli specific for the user 126a based on a combination of the current sports performance state, the target sports performance state, the retrieved at least one priori stimulus, and a trained Artificial Intelligence (AI) system, such as the local AI-based system 124 or the main AI-based system 114.

In accordance with an embodiment, the control circuitry 116 may be further configured to control the stimulus device 118 to provide the determined set of test stimuli to the user 126a for a first test duration. The plurality of stimuli may include calibrated pressure, calibrated vibration input, calibrated electric input, calibrated magnetic input, hot and cold application, touch sense-based input, sound waves, and/or the like. The plurality of stimuli may further include presenting a VR-based digital environment. The VR-based digital environment may be a combination of audio effects and visual effects. The control circuitry 116 may be configured to control the stimulus device 118 for providing the plurality of stimuli on various body portions of the users 126a. The local AI-based system 124 may provide, to the control circuitry 116, a first output that is indicative of one or more stimulus parameters and a first test duration for which the determined set of test stimuli may be applied to the user 126a. Based on the first output, the control circuitry 116 may be configured to activate the stimulus device 118 for providing the determined set of test stimuli to the user 126a for the first test duration. In accordance with an embodiment, the control circuitry 116 may be configured to activate a single stimulus sub-device or a set of stimulus sub-devices from the plurality of different stimulus sub-devices 106 at a given timepoint in the first test duration for providing the determined set of test stimuli to the user 126a.

In accordance with an embodiment, the control circuitry 116 may be further configured to determine, based on the set of internal response sensors 120, a first set of responses within the body of the user 126a from the provided set of test stimuli. The control circuitry 116 may be further configured to determine, based on the set of external response sensors 122, a second set of responses discernible on the body of the user 126a from the provided set of test stimuli. As a result of the application of the determined set of test stimuli to the user 126a for the first test duration, the first set of responses (i.e. internal responses) may be generated within the body of the user 126a and the second set of responses (i.e. external responses) may be discernible from an external surface of the body of the user 126a.

Each stimulus of the plurality of stimuli may generate a plurality of responses (for example, one or more internal responses and one or more external responses) in the body of the user 126a. Examples of the one or more internal responses may include, but are not limited to, nerve conduction, neuron firing, activity in muscles or nerves, activity in brain, alteration in blood pressure, and/or alteration in pulse rate. Examples of the one or more external responses that are discernible from external surface of the body may include, but are not limited to, locomotion and body movements, change in gestures, a body posture, a change in skin colour, and/or a voice feedback. The control circuitry 116 may be further configured to instruct the set of external response sensors 122 and the set of internal response sensors 120 to sense and measure levels of the one or more external responses and one or more internal responses generated in the body portions of the user 126a due to the application of the plurality of stimuli to the user 126a. The control circuitry 116 may be further configured to process sensor data acquired by the set of internal response sensors 120 and the set of external response sensors 122 pertaining to the first set of responses and the second set of responses, respectively.

In accordance with an embodiment, the control circuitry 116 may be further configured to detect which muscle in the body, which area in brain, or which nerve is responding each provided stimulus of the set of test stimuli. In other words, if there are any changes in the electrical brain activity and any physiological change within the body of the user 126a is ascertained based on processing of tracked data. The control circuitry 116 may be further configured to quantify the level of response measured by the set of internal response sensors 120.

In accordance with an embodiment, the control circuitry 116 may be further configured to establish an associative relationship between each stimulus-response pair from the first set of responses and the second set of responses using the local AI-based system 124. In some embodiment, for example, in the connected mode, the plurality of electronic training systems 104 may be configured to communicate the determined plurality of stimulus-response pairs to the server arrangement 102. Each stimulus-response pair is indicative of a type of stimulus that was applied and a level of each response that was generated based on the applied stimulus. The plurality of electronic training systems 104 may be further configured to communicate additional details (such as user information) pertaining to the users 126a to 126n to the server arrangement 102. The main AI-based system 114 in the connected mode (or the local AI-based system 124 in the standalone mode) may be configured to establish an associative relationship between each stimulus-response pair in the plurality of stimulus-response pairs to generate stimulus-response (SR) pair dataset (as shown in FIG. 2). In one exemplary scenario, the SR pair dataset may be a tabular database having a plurality of rows and columns. Each row may be associated with a single stimulus and may indicate the level of responses that were generated based on the corresponding single stimulus. The main AI-based system 114 in the connected mode (or the local AI-based system 124 in the standalone mode) may be configured to store the generated SR pair dataset in a memory (such as storage systems).

The control circuitry 116 may be further configured to determine a plurality of causes of similarity and variability based on the established associative relationship. The main AI-based system 114 in the connected mode (or the local AI-based system 124 in the standalone mode) may be configured to determine a plurality of causes of similarity and variability in the plurality of responses based on the established associative relationship between each of the plurality of stimulus-response pairs, user information, and the available sports knowledge. Examples of the plurality of causes of similarity and variability determined by the main AI-based system 114 in the connected mode (or the local AI-based system 124 in the standalone mode) may include, but are not limited to, age groups, sports endurance under same conditions, nutrition intake, genomic, body weight, body mass index (BMI), ailment, or the like. The main AI-based system 114 in the connected mode (or the local AI-based system 124 in the standalone mode) may be further configured to segregate the generated SR pair dataset into a plurality of training categories, for example a first training category, a second training category, and a third training category. The first training category may include a first set of stimulus-response pairs that is generally suitable for a group of people, such as all team members of a team. Similarly, the second training category may include a second set of stimulus-response pairs that is suitable for one or more specific traits, for example, similar age group, similar sports performance issues, similar sports, and/or the like. Likewise, the third training category may include a third set of stimulus-response pairs that is suitable for a specific user, i.e. segregated into subsets of stimulus-response pairs each personalized for a specific user. In accordance with an embodiment, the main AI-based system 114 may be configured to utilize supervised or unsupervised learning to find relationships among the plurality of stimulus-response pairs included in the SR pair dataset for segregation of the SR pair dataset. Thus, all the stimulus-response pairs included in the SR pair dataset may be categorized and then sub-categorized and a learning may be derived. Based on the segregated SR pair dataset, the main AI-based system 114 is trained to generate a trained neural network model (i.e., the trained main AI-based system 114).

The learnings of the trained main AI-based system 114 may be used to update the local AI-based system 124, by a transfer-learning operation from the trained main AI-based system 114 to the local AI-based system 124. For example, the segregated SR pair dataset may be communicated from the server arrangement 102 to each of the plurality of electronic training systems 104 by the transfer-learning operation. In some embodiments, the trained main AI-based system 114 may be used for deployment into a new electronic training system 104a. The main AI-based system 114 may function as a main AI and the local AI-based system 124 may function as a local AI, which may be updated as and when required by the main AI-based system 114. The local AI-based system 124 may be computationally lighter (e.g. having a smaller number of hidden layers as compared to the main AI-based system 114).

In accordance with an embodiment, the control circuitry 116 is further configured to calibrate a set of stimulus parameters for the stimulus device 118 based on a combination of the determined first set of responses, the second set of responses, the current sports performance state, the target sports performance state, and the trained artificial intelligence-based system. The stimulus device 118 is re-configured with the calibrated set of stimulus parameters to apply a new stimulus to the user 126a for a second duration. The use of the new stimulus shifts the current sports performance state towards the target sports performance state. The local AI-based system 124 may be configured to provide a second output to the control circuitry 116 based on the determination of the new stimulus. The second output may indicate the set of stimulus parameters, a second duration for which the new stimulus is to be applied to the target user 130, and one or more targeted body portions where the new stimulus is to be applied. The second duration for which the new stimulus is to be applied to the target user 130 may be greater than the first test duration. In an embodiment, the new stimulus may not be available during the training phase. In another embodiment, the new stimulus having the set of stimulus parameters is an existing stimulus that was available during the training phase. The trained electronic training system 104a may be utilized for improving a stamina and sports performance of a sportsman by the new stimulus. The trained electronic training system 104a may detect the current sports performance state of a sportsman, and continuously challenge his endurance, fitness, engagement, sports move, and the like, to improve sports performance.

In accordance with an embodiment, the stimulus device 118 may be configured to output a first digital environment around the user 126a. The first digital environment may be a human sense stimulating mixed reality environment that induces a specific stimulus to the user 126a to increase sports performance from the first spots performance state to a second sports performance state of the user 126a. In other words, the first digital environment may be electronically generated mixed reality environment that activates certain areas of brain or de-novo facilitate generation of well-being chemicals, such as endorphins. The mixed reality environment may be a combination of a virtual environment (e.g. a virtual reality environment) and tangible elements, for example, that may provide a stimulus to a human body or a portion of a human body. In one example, the stimulus device 118 may be used to provide certain tangible stimulus (e.g. heat, smell, pressure, cold, sound, a digital visualization) that acts on one or more senses of the plurality of human senses (5 senses) as a part of the first digital environment, such as audio-visual environment created by the stimulus device 118. In another example, the stimulus device 118 may be configured to generate magnetic field at different frequency as a part of the first digital environment. In an example, a sub-device of the stimulus device 118, such as a VR scene projecting sub-device, may be used to project audio-visual scenes around a user to challenge the user 126a from the current sports performance state to the target sports performance state. The audio-visual scenes projected by the VR scene projecting sub-device 106h may stimulate hearing and visual senses of the user 126a.

In accordance with an embodiment, the control circuitry 116 may be further configured to determine a response to the specific stimulus provided by the output of the first digital environment around the user 126a. Thus, the local AI-based system 124 may be further tuned to find relationships as to how an individual is responding to a provided stimulus (or the outputted digital environment). All these information pieces (i.e. relationships) may be grouped and then sub-grouped and a learning may be derived. For example, it may be found if there exists a correlation, or no correlation, or less correlation among the analysed information. Further, the process of tagging and elimination for each data point may be executed to identify correct correlation, inferences, and response(s) to provided stimulus, based on continuous training. Thus, a trained model (i.e. a trained local AI-based system 124) may be obtained.

In accordance with an embodiment, the stimulus device 118 is further configured to output a second digital environment around the user 126a with a difficulty level that is greater than the difficulty level of the first digital environment. The second digital environment is a human sense stimulating mixed reality environment that induces a new stimulus to the user 126a to increase sports performance further from the second sports performance state to a new sports performance state of the user 126a. The second digital environment may be similar to that of the first digital environment but may differ in that the second digital environment provides more challenges to the user 126a to solve. For example, the user 126a may want to set a goal to reach a target sports performance by constantly challenging self for improvement in sports performance. The electronic training system 104a provides a mechanism by which a user, such as the user 126a, is challenged to improve not only technical skills in sports, but also phycological and tactical training is imparted using various stimulus provided by the stimulus device 118. The trained electronic training system 104a may detect the current sports performance state of a sportsman, and continuously challenge his endurance, fitness, engagement, sports move, and the like, to improve sports performance.

In accordance with an embodiment, the control circuitry 116 is further configured to generate a stimulation instruction pack specific for the user 126a based on an output from a trained artificial intelligence-based system. The control circuitry is further configured to activate a single stimulus sub-device or a set of stimulus sub-devices from the plurality of different stimulus sub-devices 106 at a given timepoint in a first duration in accordance with the generated stimulation instructions pack. The stimulation instruction pack may include a type of control signal for the plurality of different stimulus sub-devices 106, a time schedule, an intensity of output, and a set of sense identifiers. The time schedule may define a specific activation time and a specific duration to generate the new stimulus in the second duration by using one or more stimulus sub-devices of the plurality of different stimulus sub-devices 106 under the control of the stimulus device 118. Each sense identifier of the set of sense identifiers may indicate a unique specific sense stimulating item to be selected for output in accordance with the time schedule. For example, a first sense identifier may indicate a specific smell for output. In such a case, the intensity of output defines what amount of liquid or gas to be sprayed and in which direction. The stimulus device 118 may be configured to select a unique specific sense stimulating item (for example, an odor generating item, a visual effects item, an audio effects item, and a touch-sense based item) for generating a single or multiple sense stimulating output/s to stimulate a specific sense/s of a plurality of human senses based on the type of control signal included in the stimulation instruction pack. Thus, based on the stimulation instruction pack, the stimulus device 118 is re-configured with the calibrated set of stimulus parameters and the new stimulus is applied to at least targeted body portions of the user 126a to enhance the current sports performance.

In accordance with an embodiment, the local AI-based system 124 and the control circuitry 116 may continue to improve and personalize the stimulus applied to the user 126a based the internal responses and the external responses exhibited by the user 126a for achieving the target sports performance state. In accordance with an embodiment, the electronic training system 104a may operate in the connected mode. While in the online mode, the electronic training system 104a may operate under the control of the server arrangement 102. Thus, based on the setting of the connected mode at the electronic training system 104a, the main AI-based system 114 may be configured to execute the same operations as executed by the local AI-based system 124 in the standalone mode.

In accordance with an embodiment, the control circuitry 116 may be further configured to determine whether an alteration is required in a training plan for the current sports performance state of the user 126a, based on the application of the new stimulus to the user 126a for the second duration and a shift in the at least one sports performance indicator of the user 126a from the current sports performance state towards the target sports performance state. The control circuitry 116 may be further configured to determine a new training plan that is different from the training plan for the current sports performance state of the user 126a based on the determination that the alteration is required. The control circuitry 116 may be further configured to communicate a training change recommendation for the user 126a to a prespecified user device 108 of a coach of the user 126a. The training change recommendation comprises the new training plan for the target sports performance state and a plurality of sports performance indicators that indicates the shift from the current sports performance towards the target sports performance state for the user 126a.

In an exemplary implementation, the control circuitry 116 may be configured to retrieve known sports performance information of a plurality of users (e.g. User 1 and user 2). The known sports performance information may be retrieved from a sports knowledge database stored locally in the electronic training system 104a, from the server arrangement 102, or directly parsed from Internet-based sources. The control circuitry 116 may be further configured to create a VR environment game based on the retrieved known sports performance information of the plurality of users. The VR environment game may then be used to train a user to learn new skills.

In another exemplary implementation, the control circuitry 116 may be configured to retrieve sports performance information of different players (e.g. players from opposite teams). The control circuitry 116 may be further configured to utilize the retrieved sports performance information to create a group-based VR which induces challenges for a user (or opponents) who uses the electronic training system 104a to train the user (or opponents). Further, in order to train a team, the control circuitry 116 may be configured to combine the sports performance information of selected or all players of the team to create a group-based VR environment for training. In an example, the control circuitry 116 may be configured to create a new VR environment by feeding information for a user who is part of training therapy into the VR environment. For example, if a first user have problems with his/her child, parent, or a second user known to the first user, the information related to the child, parent, or the second user may be fed into the VR environment to create the training therapy for the first user. In addition to improvement in sports performance, such training therapy may also find application in physical therapy, or other surgical or medical training therapies. Moreover, learned information related to sports performance learned from different players by the electronic training system 104a may be fed into the VR environment so that all the knowledge (i.e. learnings in terms of technical skills, phycological and tactical skills) may be passed to a user who may be under training. Sports performance for celebrities and famous players (e.g. Messi) is available and may be incorporated into the VR environment to create a game or a VR-based gaming environment, which in turn may be used to train a user, team members of a team, or train opponents of a sport or game.

FIG. 2 illustrates different components of a server arrangement and an electronic training system of FIG. 1, in accordance with an exemplary embodiment of the disclosure. FIG. 2 is described in conjunction with elements from FIG. 1. With reference to FIG. 2, there is shown the server arrangement 102 and the electronic training system 104a of FIG. 1. The server arrangement 102 may further include a control circuitry 202, a main storage system 204, and a network interface 206. The main storage system 204 is configured to store a sports knowledge database 208 and learned sports performance (LSP) dataset. Hereinafter, the LSP dataset stored in the main storage system 204 is designated and referred to as "the LSP dataset 210". The main AI-based system 114 may include a neural network schema 212.

The electronic training system 104a may further include a local storage system 214, a display 216, and a network interface 218. The local storage system 214 may store a sports knowledge database 220 and the LSP dataset. Hereinafter, the LSP dataset stored in the local storage system 214 is designated and referred to as "the LSP dataset 222". The display 216 may refer to a display device which may be associated with one or more UIs, such as a UI 216a. The electronic training system 104a may further include the plurality of different stimulus sub-devices 106 that may be detachably attached to the stimulus device 118 by way of a plurality of slots 224 included in the stimulus device 118. The plurality of different stimulus sub-devices 106 may include an odor emitter sub-device 106a, a vibrator sub-device 106b, a pressure sub-device 106c, an integrated digital environment (IDE) generator sub-device 106d, a magnetic field generator sub-device 106e, a touch-sense sub-device 106f, a temperature sub-device 106g, a VR scene projecting sub-device 106h, and a sound wave control sub-device 106i. A person of ordinary skill in the art will understand that the server arrangement 102 and the electronic training system 104a may also include other suitable components or systems, in addition to the components or systems which are illustrated herein to describe and explain the function and operation of the present disclosure.

The control circuitry 202 may comprise suitable logic, circuitry, and/or interfaces configured to execute instructions stored in the main storage system 204. The control circuitry 202 may be configured to implement the training phase and the operational phase (as described in FIG. 1) in association with the electronic training system 104a. The control circuitry 202 may be configured to generate the LSP dataset 210 in the training phase (as described in FIG. 1). The control circuitry 202 may be configured to convert the primary information and the supplementary information into the AI-based system-readable data format. Examples of the control circuitry 202 may be an X86-based processor, a RISC processor, an ASIC processor, a CISC processor, a microcontroller, a CPU, a GPU, a state machine, and/or other processors or circuits.

The main storage system 204 may comprise suitable logic, circuitry, and/or interfaces configured to store a machine code and instructions with at least one code section executable by the control circuitry 202. The main storage system 204 may store the sports knowledge database 208 and the LSP dataset 210. The sports knowledge database 208 may include details pertaining to available sports literature. For example, the sports knowledge database 208 may include known technical skills, shots, or conditioning required for different outdoor or indoor sports, extracted information from sports performance related e-books, coaching case studies, research papers, sports psychology, physiology (including nutrition) focused on preparing a user for competition in a sporting activity. The main storage system 204 may store one or more machine learning algorithms (for example, deep learning algorithms or other types of artificial intelligence algorithms) that enable the main AI-based system 114 to implement the training phase based on the sports knowledge database 208 and the LSP dataset 210 that is specific for a specific user. Examples of implementation of the main storage system 204 may include, but are not limited to, an Electrically Erasable Programmable Read-Only Memory (EEPROM), a Random Access Memory (RAM), a Read Only Memory (ROM), a Hard Disk Drive (HDD), a Flash memory, a Secure Digital (SD) card, a Solid-State Drive (SSD), and/or a CPU cache memory.

The network interface 206 may comprise suitable logic, circuitry, interfaces, and/or code that may be configured to connect and communicate with a plurality of devices in the network environment 100, for example, with the electronic training system 104a. The network interface 206 may implement known technologies to support wireless communication. The network interface 206 may include, but are not limited to an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer. The network interface 206 may communicate via offline and online wireless communication with networks, such as the Internet, an Intranet, and/or a wireless network, such as a cellular telephone network, a wireless local area network (WLAN), personal area network, and/or a metropolitan area network (MAN). The wireless communication may use any of a plurality of communication standards, protocols and technologies, such as Global System for Mobile Communications (GSM), Enhanced Data GSM Environment (EDGE), wideband code division multiple access (W-CDMA), code division multiple access (CDMA), LTE 4G, 5G, time division multiple access (TDMA), Bluetooth, Wireless Fidelity (Wi-Fi) (such as IEEE 802.11, IEEE 802.11b, IEEE 802.11g, IEEE 802.11n, and/or any other IEEE 802.11 protocol), voice over Internet Protocol (VoIP), Wi-MAX, Internet-of-Things (IoT) technology, Machine-Type-Communication (MTC) technology, a protocol for email, instant messaging, and/or Short Message Service (SMS).

The neural network schema 212 may refer to a neural network architecture having a number of layers, such as an input layer, an output layer, and intermediate layers that operates on data received at the input layer to generate corresponding output at the output layer. The neural network schema 212 may also be referred to as a neural network model. The neural network schema 212 of the main AI-based system 114 may be provided with unlabeled, uncategorized data of stimulus-response pairs in the AI-based system-readable data format from the plurality of electronic training systems 104 and the main AI-based system 114 may act on the data to automatically find structure and pattern in the stimulus-response pairs by extracting features and analyzing its pattern to draw inferences.

The local storage system 214 includes suitable logic, circuitry, and/or interfaces that may be configured to store machine code and/or instructions with at least one code section executable by the control circuitry 116. The local storage system 214 may store a sports knowledge database 220 and an LSP dataset 222. The sports knowledge database 220 may be similar to the sports knowledge database 208 and may include details pertaining to the available sports literature. The LSP dataset 222 is a local instance of the LSP dataset 210 that is specific for a user, such as the user 126a. The local storage system 214 may store one or more machine learning algorithms (for example, deep learning algorithms or other types of artificial intelligence algorithms) that enable the local AI-based system 124 to execute one or more corresponding operations during the connected mode and standalone mode. Examples of implementation of the local storage system 214 may include, but are not limited to, an EEPROM, a RAM, a ROM, an HDD, a Flash memory, an SD card, an SSD, and/or a CPU cache memory.

The display 216 may comprise suitable logic, circuitry, and/or interfaces configured to receive the user information via the user interface 216a and render the first integrated visual motion model for the user 126a, who needs to improve sports performance. In accordance with an embodiment, the display 216 may be a touch screen display that may receive an input from the user 126a or the operator of the electronic training system 104a. Examples of the display 216 may include, but are not limited to, a see-through display, a projection-based display, a smart-glass display, and/or an electro-chromic display. The display 216 may be a transparent or a semi-transparent display screen. The user interface 216a may be rendered at the display 216 under the control of the control circuitry 116.

The network interface 218 may comprise suitable logic, circuitry, interfaces, and/or code that may be configured to connect and communicate with a plurality of devices in the network environment 100 (FIG. 1). The network interface 218 may be similar to that of the network interface 206.

The plurality of slots 224 may correspond to attachment means for the stimulus device 118 for attaching one or more of the plurality of different stimulus sub-devices 106 as and when required. For example, in a modular arrangement, the odor emitter sub-device 106a, the vibrator sub-device 106b, the pressure sub-device 106c, the IDE generator sub-device 106d, the magnetic field generator sub-device 106e, the touch-sense sub-device 106f, the temperature sub-device 106g, the VR scene projecting sub-device 106h, and the sound wave control sub-device 106i may be detachably attached to the stimulus device 118 by using the plurality of slots 224.

The odor (scent) emitter sub-device 106a may comprise suitable logic, circuitry, and/or interfaces configured to emit different types of odor as output. For example, the odor emitter sub-device 106a may be configured to spray liquid or gas for emitting the different types of odor. The intensity of the output may be controlled based on an amount of the liquid or gas sprayed. The odor emitted by the odor emitter sub-device 106a may stimulate smelling sense of a user.

The vibrator sub-device 106b may comprise suitable logic, circuitry, and/or interfaces configured to generate vibrations as output. The intensity of the output may be controlled by controlling the intensity of generated vibrations. The vibrations generated by the vibrator sub-device 106b may stimulate touch sense of a user. The pressure sub-device 106c may comprise suitable logic, circuitry, and/or interfaces configured to provide calibrated pressure as output. The intensity of the output may be controlled by controlling the intensity of the pressure. The pressure provided by the pressure sub-device 106c may stimulate the touch sense of a user.

The IDE generator sub-device 106d may comprise suitable logic, circuitry, interfaces, and/or code that may be configured to output a customized integrated digital environment around a user as output. The IDE generator sub-device 106d may control the customized digital environment by use of various modules and devices, of the electronic training system 104a. Examples of implementations of the IDE generator 106d may be an X86-based processor, a GPU, a RISC processor, an ASIC processor, a CISC processor, a microcontroller, a CPU, a specialized hardware generator, and/or other mixed reality control circuits.

The magnetic field generator sub-device 106e may comprise suitable logic, circuitry, and/or interfaces configured to generate magnetic field around a user as output. The touch-sense sub-device 106f may comprise suitable logic, circuitry, and/or interfaces configured to stimulate touch sense of a user.

The temperature sub-device 106g may comprise suitable logic, circuitry, and/or interfaces configured to provide hot and cold application to a user. In one example, the temperature sub-device 106g may include IR lamps for providing hot application to the user.

The VR scene projecting sub-device 106h may comprise suitable logic, circuitry, and/or interfaces configured to project audio-visual scenes around a user to challenge the user from a current sports performance state to a target sports performance state. The audio-visual scenes projected by the VR scene projecting sub-device 106h may stimulate hearing and visual senses of the user. Examples of implementations of the VR scene projecting sub-device 106h may be an X86-based processor, a GPU, a RISC processor, an ASIC processor, a CISC processor, a microcontroller, a CPU, a specialized hardware generator, and/or other control circuits.

The sound wave control sub-device 106i may comprise suitable logic, circuitry, and/or interfaces configured to generate sound waves as output. The sound waves generated by the sound wave control sub-device 106i may stimulate hearing sense of a user. It will be apparent to those of skill in the art that the plurality of different stimulus sub-devices 106 may include other sub-devices as well, for example, an exercise mechanism that enables planned movement in various body portions (for example, arms, wrists, legs, thighs, neck, feet, and/or back) of the user for exercising.

Figure 3A:
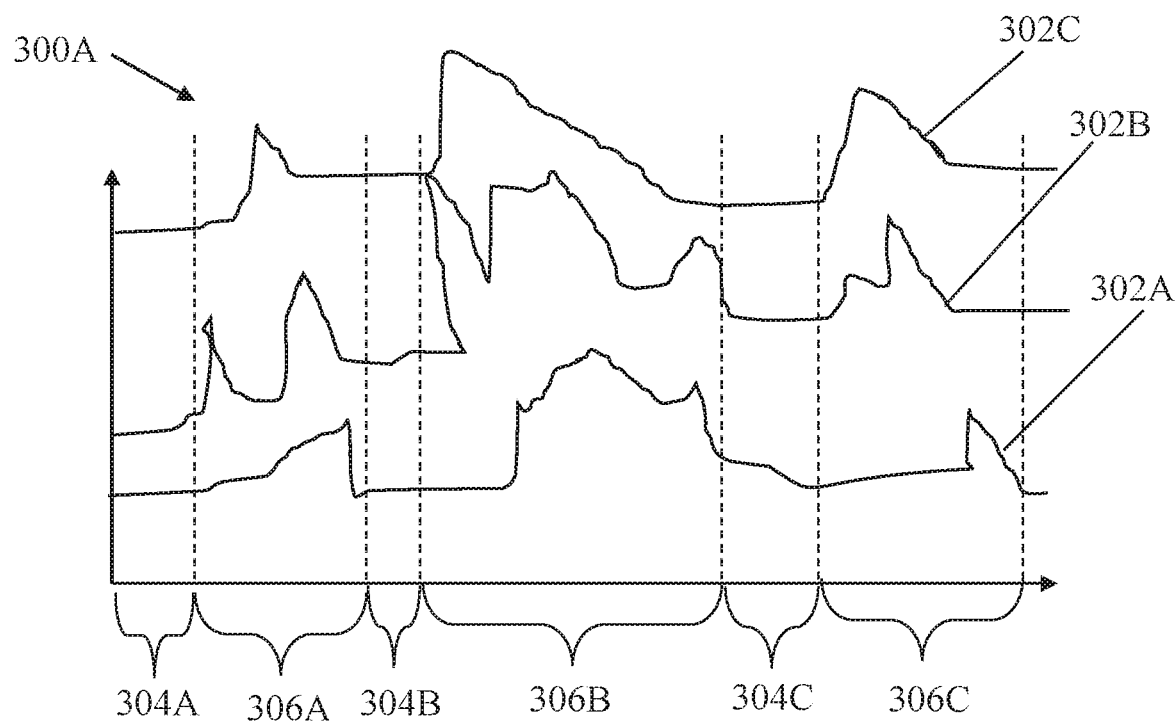
FIG. 3A is a diagram that illustrates an exemplary annotation of tracked data in a sporting event as a set of period-of-relevance and a set of period-of-irrelevance, in accordance with an embodiment of the disclosure.

FIG. 3A illustrates an exemplary annotation of tracked data in a sporting event as a set of period-of-relevance and a set of period-of-irrelevance, in accordance with an embodiment of the disclosure. FIG. 3A is described in conjunction with elements from FIGS. 1 to 2. With reference to FIG. 3A, there is shown a graphical representation 300A of an exemplary tracked data for an exemplary time interval for annotation of the tracked data in a sporting event for the purpose of electronic evaluation of sports performance of a user (such as the user 126a of FIG. 1). In the graphical representation 300A, there is further shown a first signal 302A to denote tracked body movements, a second signal 302B to denote tracked electrical brain activity, and a third signal 302C to denote tracked physiological changes for the user 126a (not shown) in a given sporting event.

In accordance with an embodiment, the control circuitry 116 may be configured to annotate tracked data in the sporting event as a set of period-of-relevance, such as a first period-of-relevance 306A, a second period-of-relevance 306B, and a third period-of-relevance 306C, and a set of period-of-irrelevance, such as a first period-of-irrelevance 304A, a second period-of-irrelevance 304B, and a third period-of-irrelevance 304C. The tracked data is segregated and annotated into periods-of-relevance and irrelevance based on a correlation in the tracked body movements, the tracked electrical brain activity, and the tracked physiological changes for the user 126a in the given sporting event. The annotated tracked data as the set of period-of-relevance for the given sporting event may be used as training dataset for the local-AI based system 124.

Figure 3B:
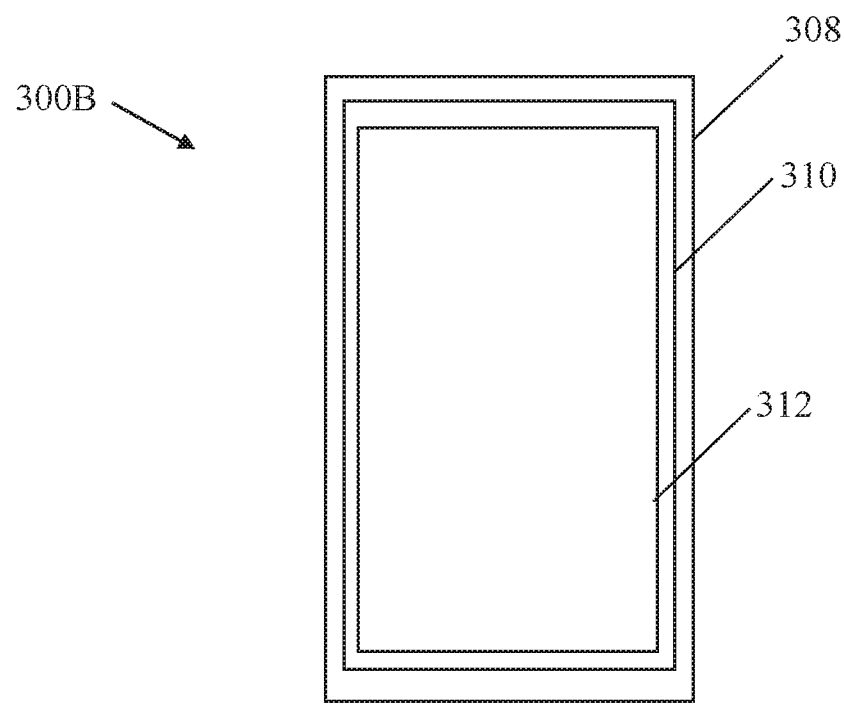
FIG. 3B is a diagram that illustrates an exemplary first integrated visual motion model, in accordance with another embodiment of the disclosure.

FIG. 3B illustrates an exemplary first integrated visual motion model, in accordance with another embodiment of the disclosure. FIG. 3A is described in conjunction with elements from FIGS. 1, 2, and 3A. With reference to FIG. 3B, there is shown an exemplary block diagram to explain a first integrated visual motion model 300B.

In accordance with an embodiment, the control circuitry 116 may be configured to output the first integrated visual motion model 300B on the display 216 based on annotated tracked data in the set of period-of-relevance. The integrated visual motion model 300B comprises a first visual representation 308 of the tracked locomotion and the body movements, a second visual representation 310 of the tracked electrical brain activity, and a third visual representation 312 of the tracked physiological changes in the body that are merged in the first integrated visual motion model 300B and time-controlled at output such that the first sports performance state of the user 126a for the given sporting event is discernible by a viewer.

In accordance with an embodiment, the first integrated visual motion model 300B is a three-dimensional (3D) computer graphic model (hereinafter referred to as 3D model) of the user 126a that reflects the external as well as internal changes in a meaningful synchronization during the set of period-of-relevance in the given sporting event. The first integrated visual motion model 300B may be a visual scene that depicts metadata and meaningful information that indicates various reasons and causes that led to the first sports performance state of the user 126a assigned by the control circuitry 116. The first integrated visual motion model 300B provides a synergistic view to explore combined effects and a holistic view of changes in the tracked locomotion and the body movements, the tracked electrical brain activity, and the tracked physiological changes in the body that is easy to understand for a viewer, such as the coach of the user 126a or the user 126a. For example, when a movement is performed by the user 126a, for example, kicking a soccer ball, not only the motion of kick, is visible in the first visual representation 308, but also some portion of the first visual representation is turned transparent so that internal changes, such as blood flow, VO2, heart rate, lactic acid formation in muscle is visible via the second layer, such as the second visual representation 310 as well as electrical brain activity or neuron firing via the third visual representation 312 of the user 126a is visible too. Further, meaning of such visible data in terms of what is considered a good performance and where there is scope of improvement is also determined and rendered beside the first integrated visual motion model 300B based on the LSP dataset 222. A reference to previous performance of the user 126a in a previous sporting event, in which the user 126a was comparatively better or poor in terms of sports performance state for the similar type of game situation (e.g. similar motion of limbs during a kick of the soccer ball) is also automatically retrieved and presented on the user interface 216a of the display 216. This provides a holistic and enhanced understanding of the sports performance state for each relevant action in the set of period-of-relevance in the given sporting event.

Figure 3C:
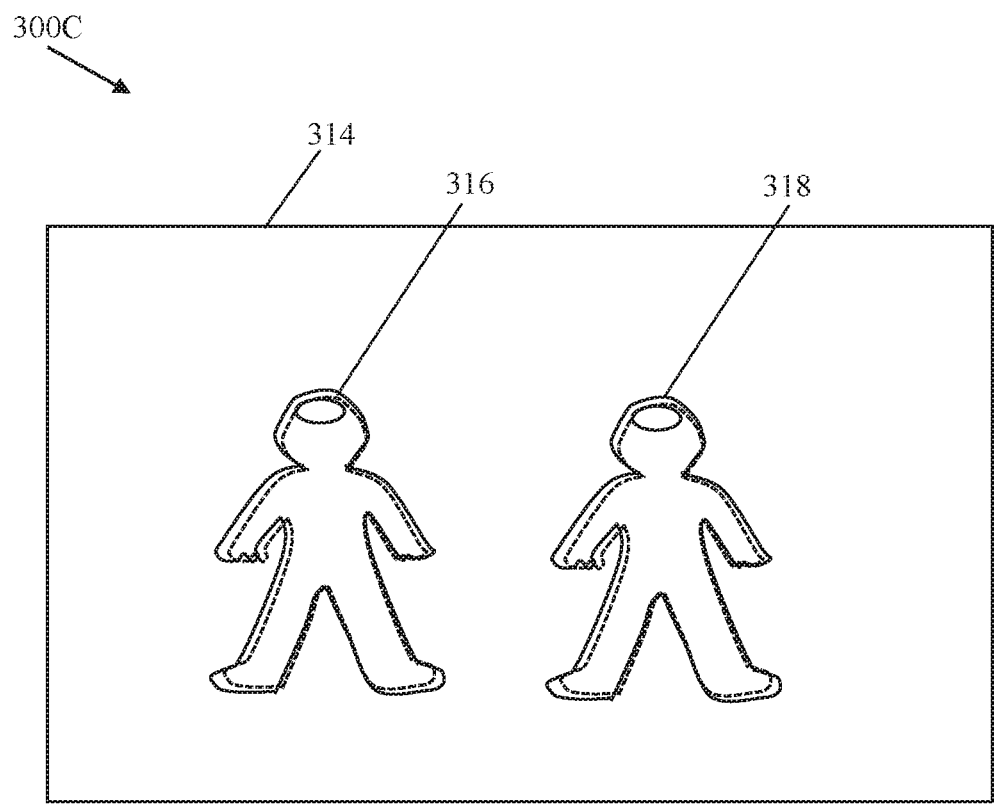
FIG. 3C is a diagram that illustrates an exemplary scenario for implementation of the electronic training system of FIG. 1, in accordance with an exemplary embodiment of the disclosure.
Figure 4A:
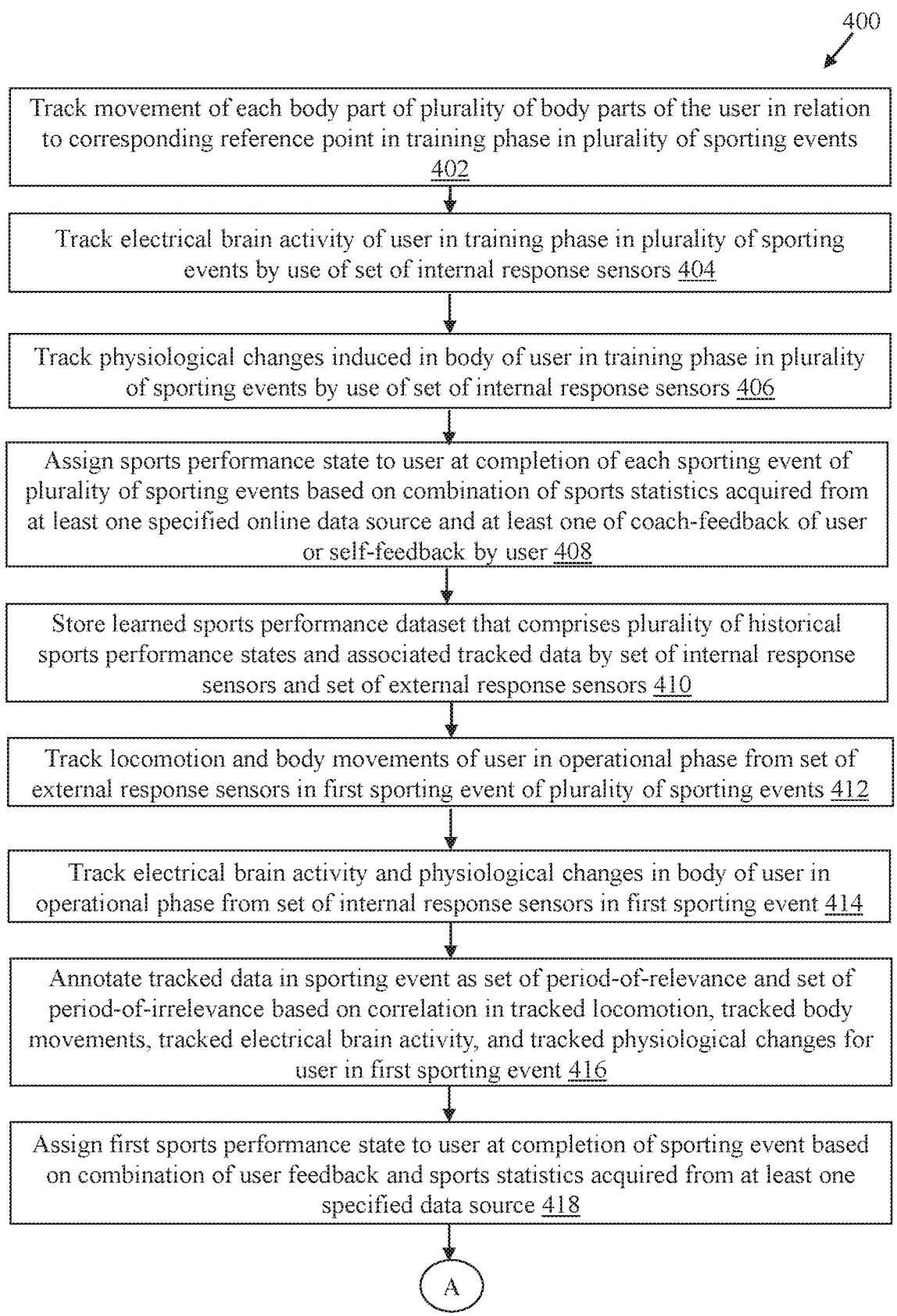
FIGS. 4A, 4B, 4C, and 4D collectively, is a flowchart that illustrates a method for electronic evaluation and feedback of sports performance, in accordance with an exemplary embodiment of the disclosure.
Figure 4B:
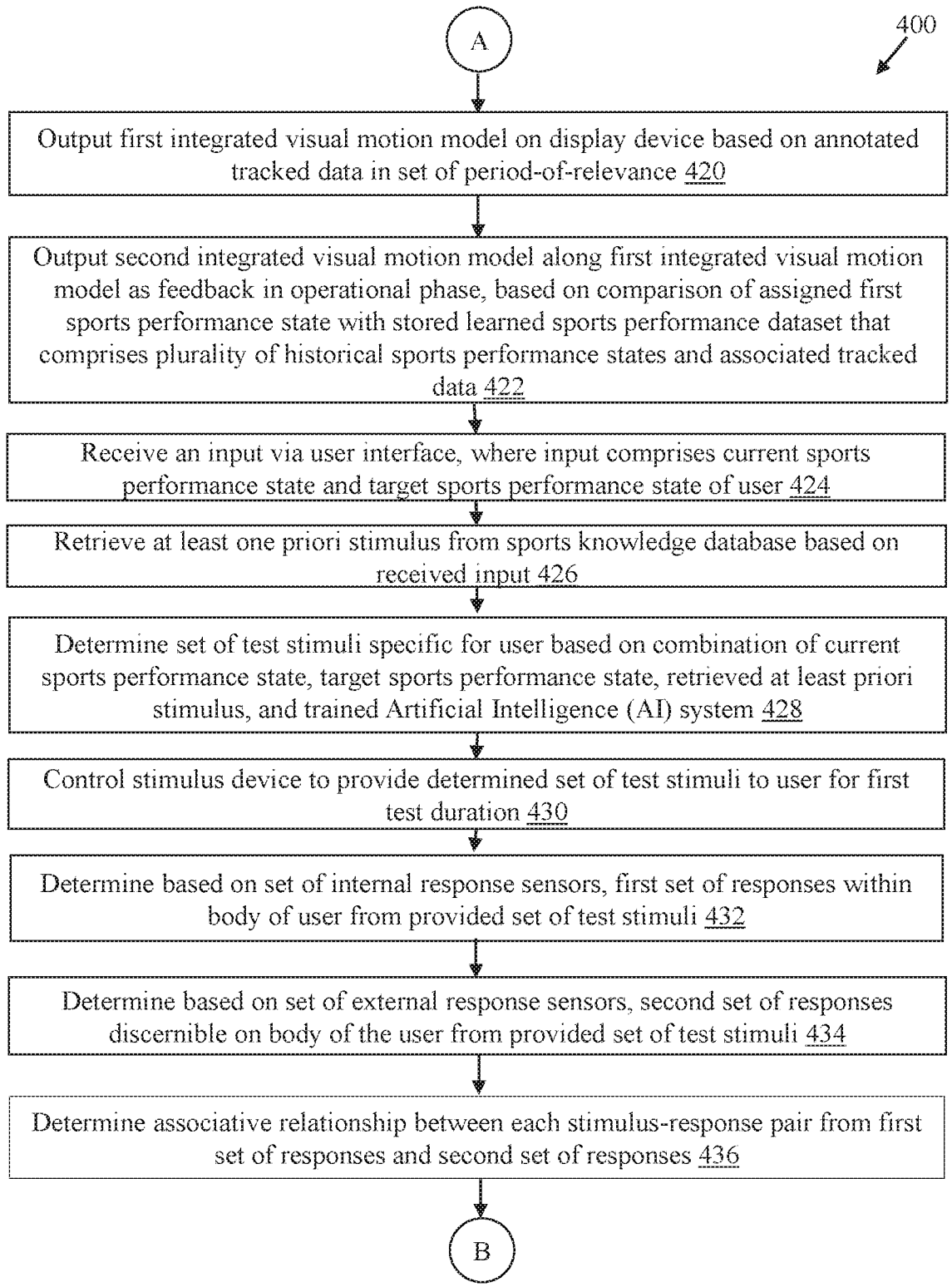
Figure 4C:
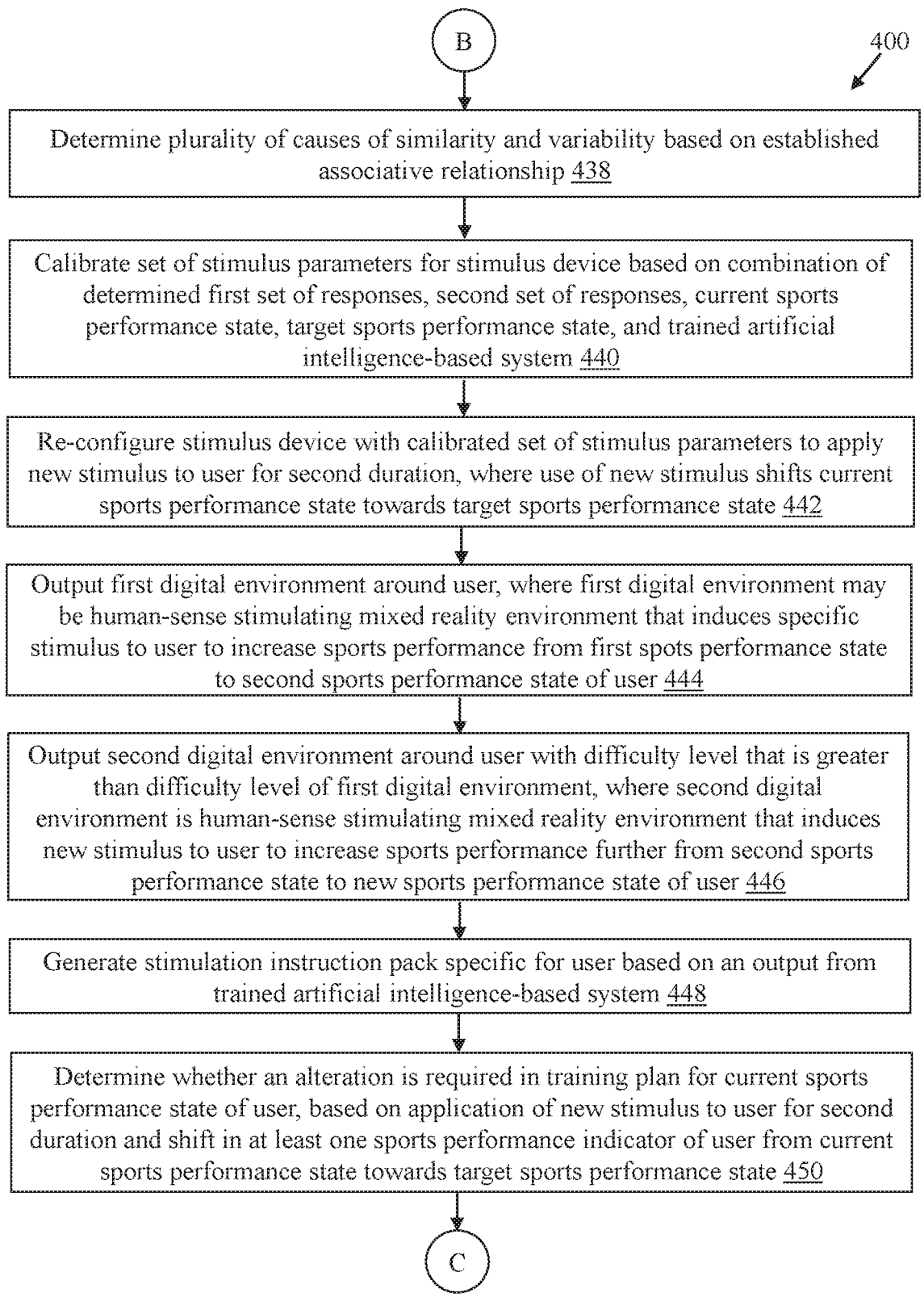
Figure 4D:
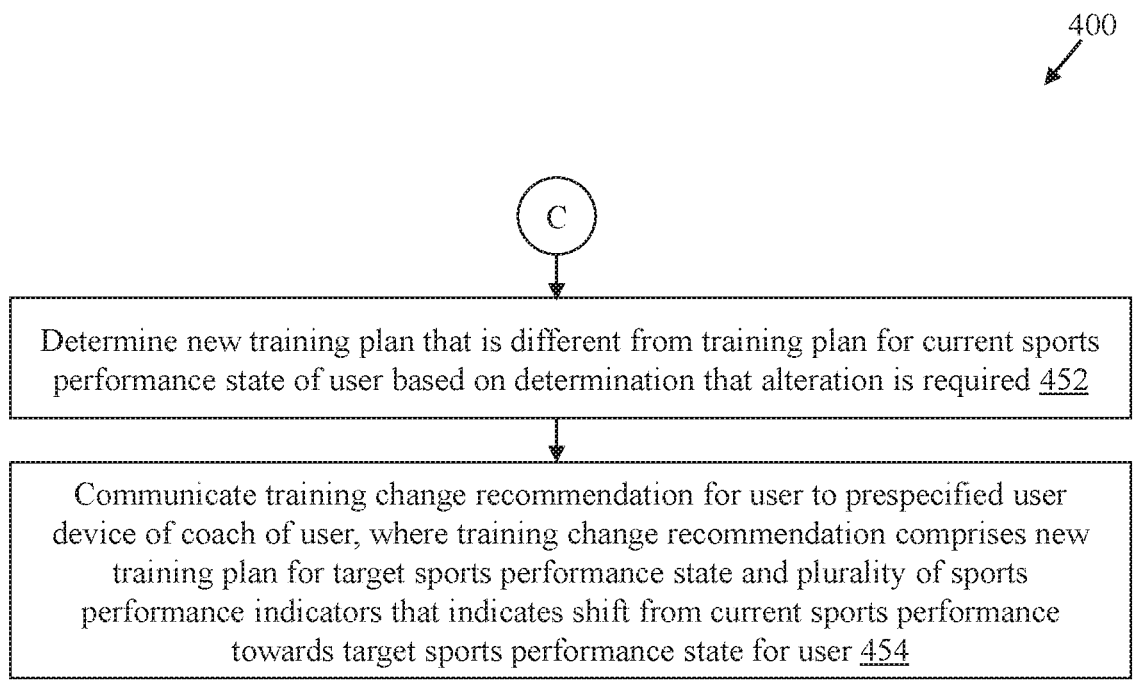

FIG. 3C illustrates an exemplary scenario for implementation of the electronic training system of FIG. 1, in accordance with an exemplary embodiment of the disclosure. FIG. 3C is described in conjunction with elements from FIGS. 1, 2, 3A, and 3B. With reference to FIG. 3C, there is shown an exemplary scenario 300C that depicts a user interface 314 with a first integrated visual motion model 316 along with a second integrated visual motion model 316 rendered side-by-side for providing feedback to the user 126a to improve sports performance. The first integrated visual motion model 316 may correspond to the first integrated visual motion model 300B of FIG. 3B. The user interface 314 may correspond to the user interface 216a.

In accordance with an embodiment, the control circuitry 116 in the operational phase may be further configured to output the second integrated visual motion model 316 along the first integrated visual motion model 314 as feedback via the user interface 314. The second integrated visual motion model 316 is outputted based on a comparison of the assigned first sports performance state with the stored learned sports performance dataset 222 (or LSP dataset 210) that comprises the plurality of historical sports performance states and associated tracked data. The second integrated visual motion model 316 indicates a set of positive performance activities and a set of negative performance activities in a given sporting event. In this case, the second integrated visual motion model 316 is retrieved from the LSP dataset 222 or 210 based on a similar action performed to achieve a similar result, such as a goal in a soccer match from a given positions of players in a field. In one example, the second integrated visual motion model 316 may be one of the sports' performance of the same user 126a who may have played better in one of previous sporting events as compared to current sporting event. Thus, a side-by-side visual comparison of the same user 126a acts as an evidence and a practical feedback what works well (i.e. a positive performance activity) and what does not work well (i.e. a negative performance activity) under a similar situation in a sporting event for the user 126a. Such FIGS. 4A, 4B, 4C, and 4D collectively, is a flowchart that illustrates a method for electronic evaluation and feedback of sports performance, in accordance with an exemplary embodiment of the disclosure. FIGS. 4A to 4D are described in conjunction with elements from FIGS. 1, 2, and 3A to 3C. With reference to FIGS. 4A, 4B, 4C, and 4D there is shown a flowchart 400 comprising exemplary operations 402 through 454 executed by the electronic training system 104a.

At 402, each body part of a plurality of body parts of the user 126a in relation to a corresponding reference point may be tracked in a training phase in a plurality of sporting events from a combination of the set of external response sensors 122 and the set of internal response sensors 120. The reference point for a specific body part may be selected based on a current position of the specific body part that is tracked. At 404, electrical brain activity of the user 126a may be tracked in the training phase in the plurality of sporting events by use of the set of internal response sensors 120.

At 406, physiological changes induced in the body of the user 126a may be tracked in the training phase in the plurality of sporting events by use of the set of internal response sensors 120. At 408, a sports performance state may be assigned to the user 126a at completion of each sporting event of the plurality of sporting events based on a combination of sports statistics acquired from at least one specified online data source and at least one of a coach-feedback of the user or a self-feedback by the user 126a.

At 410, a learned sports performance dataset 210 that comprises a plurality of historical sports performance states and associated tracked data by the set of internal response sensors 120 and the set of external response sensors 122, may be stored. The learned sports performance dataset may be stored in the local storage system 214 or the server arrangement 102. The plurality of historical sports performance states corresponds to the assigned sports performance state to the user at completion of each sporting event of the plurality of sporting events. At 412, locomotion and body movements of the user 126a may be tracked in an operational phase from the set of external response sensors 122 in a first sporting event of the plurality of sporting events (i.e. a new sporting event in the operational phase after the training phase).

At 414, electrical brain activity and physiological changes in a body of the user 126a may be further tracked from the set of internal response sensors 120 in the first sporting event (i.e. the new sporting event). At 416, tracked data in the first sporting event may be annotated as a set of period-of-relevance and a set of period-of-irrelevance based on a correlation in the tracked locomotion, the tracked body movements, the tracked electrical brain activity, and the tracked physiological changes for the user in the first sporting event.

At 418, a first sports performance state may be assigned to the user 126a at completion of the first sporting event (e.g. the new sporting event) based on a combination of a user feedback and sports statistics acquired from at least one specified data source. At 420, a first integrated visual motion model may be outputted on a display device (e.g. the display 216) based on annotated tracked data in the set of period-of-relevance. The first integrated visual motion model may include a first visual representation of the tracked locomotion and the body movements, a second visual representation of the tracked electrical brain activity, and a third visual representation of the tracked physiological changes in the body that are merged in the first integrated visual motion model and time-controlled at output such that the first sports performance state of the user 126a for the sporting event is discernible by a viewer.

At 422, a second integrated visual motion model may be outputted along the first integrated visual motion model as feedback in the operational phase, based on a comparison of the assigned first sports performance state with the stored learned sports performance dataset that comprises the plurality of historical sports performance states and associated tracked data. The second integrated visual motion model may indicate a set of positive performance activities and a set of negative performance activities in relation to the first sports performance state of the user 126a for the first sporting event (i.e. the new sporting event) or a second sporting event (e.g. another sporting event different than the first sporting event in the operational phase) of the plurality of sporting events. At 424, an input may be received via a user interface, where the input comprises a current sports performance state and a target sports performance state of the user 126a.

At 426, at least one priori stimulus may be retrieved from a sports knowledge database 220 based on the received input. At 428, a set of test stimuli specific for the user 126a may be determined based on a combination of the current sports performance state, the target sports performance state, the retrieved at least one priori stimulus, and a trained Artificial Intelligence (AI) system.

At 430, the stimulus device 118 may be controlled to provide the determined set of test stimuli to the user 126a for a first test duration. At 432, based on the set of internal response sensors 120, a first set of responses may be determined within the body of the user 126a from the provided set of test stimuli.

At 434, based on the set of external response sensors 122, a second set of responses discernible on the body of the user 126a from the provided set of test stimuli may be determined. At 436, an associative relationship may be determined between each stimulus-response pair from the first set of responses and the second set of responses.

At 438, a plurality of causes of similarity and variability may be determined based on the established associative relationship. At 440, a set of stimulus parameters may be calibrated for the stimulus device 118 based on a combination of the determined first set of responses, the second set of responses, the current sports performance state, the target sports performance state, and the trained artificial intelligence-based system (such as the local AI-based system 124 or the main AI-based system 114).

At 442, the stimulus device 118 may be re-configured with the calibrated set of stimulus parameters to apply a new stimulus to the user 126a for a second duration, where the use of the new stimulus shifts the current sports performance state towards the target sports performance state. At 444, a first digital environment may be outputted around the user 126a, where the first digital environment may be a human-sense stimulating mixed reality environment that induces a specific stimulus to the user 126a to increase sports performance from the first spots performance state to a second sports performance state of the user 126a.

At 446, a second digital environment may be outputted around the user 126a with a difficulty level that is greater than the difficulty level of the first digital environment, where the second digital environment is a human-sense stimulating mixed reality environment that induces a new stimulus to the user 126a to increase sports performance further from the second sports performance state to a new sports performance state of the user 126a. At 448, a stimulation instruction pack specific for the user 126a may be generated based on an output from a trained artificial intelligence-based system. The control circuitry 116 may be further configured to activate a single stimulus sub-device or a set of stimulus sub-devices from the plurality of different stimulus sub-devices 106 at a given timepoint in a first duration in accordance with the generated stimulation instruction pack. The physical stimulation instructions pack may include the type of control signal for the plurality of different stimulus sub-devices 106, the time schedule that defines the specific activation time and the specific duration to generate the output in the second duration, the intensity of the output, and the set of sense identifiers.

At 450, it may be determined whether an alteration is required in a training plan for the current sports performance state of the user 126a, based on the application of the new stimulus to the user for the second duration and a shift in the at least one sports performance indicator of the user 126a from the current sports performance state towards the target sports performance state. At 452, a new training plan may be determined that is different from the training plan for the current sports performance state of the user 126a based on the determination that the alteration is required.

At 454, a training change recommendation for the user 126a may be communicated to a prespecified user device of a coach of the user 126a, where the training change recommendation comprises the new training plan for the target sports performance state and a plurality of sports performance indicators that indicates the shift from the current sports performance towards the target sports performance state for the user 126a. The control may pass to end.

The electronic training system 104a provides a platform by which a user, such as the user 126a, is challenged to improve not only technical skills in sports, but also phycological and tactical skills imparted using various stimulus provided by the stimulus device 118. The trained electronic training system 104a may detect the current sports performance state of a sportsman, and continuously challenge his endurance, fitness, engagement, sports move, and the like, to improve sports performance.

In accordance with another embodiment, a deep learning algorithm or neural network model (NM) such as a convolutional neural network (CNN model) may be utilized to learn and copy or replicate the actions of each player in real life in order to create a corresponding virtual player for the virtual environment. Information for real games that a player has played may be captured and fed to the deep learning algorithm and used to create the corresponding virtual player. This may be done for several players. The output from the deep learning algorithm may be used to create and/or program one or more virtual players, which in turn may be utilized to create the virtual environment. Other examples of the deep learning algorithm or neural network model may comprise a deep neural network (DNN), a recurrent neural network (RNN), a CNN-recurrent neural network (CNN-RNN), R-CNN, Fast R-CNN, Faster R-CNN, an artificial neural network (ANN), (You Only Look Once) YOLO network, a Long Short Term Memory (LSTM) network based RNN, CNN+ANN, LSTM+ANN, a gated recurrent unit (GRU)-based RNN, a fully connected neural network, a Connectionist Temporal Classification (CTC) based RNN, a deep Bayesian neural network, a Generative Adversarial Network (GAN), and/or any combination thereof.

Various embodiments of the disclosure may provide a non-transitory computer-readable medium having stored thereon, computer implemented instruction that when executed by a computing device causes a device to execute operations similar to the operations disclosed herein for the operation of the electronic training system 124a.

While various embodiments described in the present disclosure have been described above, it should be understood that they have been presented by way of example, and not limitation. It is to be understood that various changes in form and detail can be made therein without departing from the scope of the present disclosure. In addition to using hardware (e.g., within or coupled to a central processing unit ("CPU" or processor), microprocessor, micro controller, digital signal processor, processor core, system on chip ("SOC") or any other device), implementations may also be embodied in software (e.g. computer readable code, program code, and/or instructions disposed in any form, such as source, object or machine language) disposed for example in a non-transitory computer-readable medium configured to store the software. Such software can enable, for example, the function, fabrication, modeling, simulation, description and/or testing of the apparatus and methods describe herein. For example, this can be accomplished through the use of general program languages (e.g., C, C++), hardware description languages (HDL) including Verilog HDL, VHDL, and so on, or other available programs. Such software can be disposed in any known non-transitory computer-readable medium, such as semiconductor, magnetic disc, or optical disc (e.g., CD-ROM, DVD-ROM, etc.). The software can also be disposed as computer data embodied in a non-transitory computer-readable transmission medium (e.g., solid state memory any other non-transitory medium including digital, optical, analogue-based medium, such as removable storage media). Embodiments of the present disclosure may include methods of providing the apparatus described herein by providing software describing the apparatus and subsequently transmitting the software as a computer data signal over a communication network including the internet and intranets.

It is to be further understood that the system described herein may be included in a semiconductor intellectual property core, such as a microprocessor core (e.g., embodied in HDL) and transformed to hardware in the production of integrated circuits. Additionally, the system described herein may be embodied as a combination of hardware and software. Thus, the present disclosure should not be limited by any of the above-described exemplary embodiments, but should be defined only in accordance with the following claims and their equivalents.

What is claimed is:

1. An electronic training system, comprising:
a set of external response sensors configured to sense and measure an external change discernible on a body of a user;
a set of internal response sensors configured to sense and measure an internal change within the body of the user; and
control circuitry in an operational phase is configured to:
track locomotion and body movements of a user from the set of external response sensors in a first sporting event of a plurality of sporting events;
track electrical brain activity and physiological changes in a body of the user from the set of internal response sensors in the first sporting event;
annotate tracked data in the first sporting event as a set of period-of-relevance and a set of period-of-irrelevance based on a correlation in the tracked locomotion, the tracked body movements, the tracked electrical brain activity, and the tracked physiological changes for the user in the first sporting event;
assign a first sports performance state to the user at completion of the first sporting event based on a combination of a user feedback and sports statistics acquired from at least one specified data source; and output a first integrated visual motion model on a display device based on annotated tracked data in the set of period-of-relevance, wherein the first integrated visual motion model comprises a first visual representation of the tracked locomotion and the body movements, a second visual representation of the tracked electrical brain activity, and a third visual representation of the tracked physiological changes in the body that are merged in the first integrated visual motion model and time-controlled at output such that the first sports performance state of the user for the first sporting event is discernible by a viewer.

2. The electronic training system according to claim 1, wherein the control circuitry in a training phase is further configured to track movements of each body part of a plurality of body parts of the user in relation to a corresponding reference point in the plurality of sporting events from a combination of the set of external response sensors and the set of internal response sensors, wherein the corresponding reference point for a specific body part is selected based on a current position of the specific body part that is tracked.

3. The electronic training system according to claim 2, wherein the control circuitry in the training phase is further configured to:
track the electrical brain activity of the user in the plurality of sporting events by use of the set of internal response sensors;
track physiological changes induced in the body of the user in the plurality of sporting events by use of the set of internal response sensors; and
assign a sports performance state to the user at completion of each sporting event of the plurality of sporting events based on a combination of sports statistics acquired from at least one specified online data source and at least one of a coach- feedback of the user or a self-feedback by the user.

4. The electronic training system according to claim 3, further comprises a storage system configured to store a learned sports performance dataset that comprises a plurality of historical sports performance states and associated tracked data by the set of internal response sensors and the set of external response sensors, wherein plurality of historical sports performance states corresponds to the assigned sports performance state to the user at completion of each sporting event of the plurality of sporting events.

5. The electronic training system according to claim 4, wherein the control circuitry in the operational phase is further configured to output a second integrated visual motion model along the first integrated visual motion model as feedback, based on a comparison of the assigned first sports performance state with the stored learned sports performance dataset that comprises a plurality of historical sports performance states and associated tracked data, and wherein the second integrated visual motion model indicates a set of positive performance activities and a set of negative performance activities in relation to the first sports performance state of the user for the first sporting event or a second sporting event of the plurality of sporting events.

6. The electronic training system according to claim 1, further comprises a stimulus device, wherein the stimulus device is configured to output a first digital environment around the user, wherein the first digital environment is a human-sense stimulating mixed reality environment that induces a specific stimulus to the user to increase sports performance from the first sports performance state to a second sports performance state of the user.

7. The electronic training system according to claim 6, wherein the stimulus device is further configured to output a second digital environment around the user with a difficulty level that is greater than the difficulty level of the first digital environment, wherein the second digital environment is a human-sense stimulating mixed reality environment that induces a new stimulus to the user to increase sports performance further from the second sports performance state to a new sports performance state of the user.

8. The electronic training system according to claim 6, wherein the stimulus device is a human senses stimulator device, wherein the stimulus device comprises a plurality of slots to detachably attach a plurality of different stimulus sub-devices in the plurality of slots in a modular arrangement.

9. The electronic training system according to claim 6, wherein each stimulus sub-device of a plurality of different stimulus sub-device is selected from at least one of: a pressure sub-device, a temperature sub-device, a vibrator sub-device, a sound wave control sub-device, a virtual reality (VR) scene projecting sub-device, an odor emitter sub-device, a touch-sense sub-device, a magnetic field generator sub-device, and an integrated digital environment generator sub-device.

10. The electronic training system according to claim 9, wherein the control circuitry is further configured to generate a stimulation instructions pack specific for the user based on an output from a trained artificial intelligence-based system, wherein the control circuitry is further configured to activate a single stimulus sub-device or a set of stimulus sub-devices from a plurality of different stimulus sub-devices at a given timepoint in a first duration in accordance with the generated stimulation instructions pack.

11. The electronic training system according to claim 6, wherein the control circuitry is further configured to:
receive an input via a user interface, wherein the input comprises a current sports performance state and a target sports performance state of the user;
retrieve at least one priori stimulus from a sports knowledge database based on the received input; and
determine a set of test stimuli specific for the user based on a combination of the current sports performance state, the target sports performance state, the retrieved at least one priori stimulus, and a trained Artificial Intelligence (AI) system.

12. The electronic training system according to claim 11, wherein the control circuitry is further configured to control the stimulus device to provide the determined set of test stimuli to the user for a first test duration.

13. The electronic training system according to claim 12, wherein the control circuitry is further configured to:
determine, based on the set of internal response sensors, a first set of responses within the body of the user from the provided set of test stimuli; and
determine, based on the set of external response sensors, a second set of responses discernible on the body of the user from the provided set of test stimuli.

14. The electronic training system according to claim 13, wherein the control circuitry is further configured to:
calibrate a set of stimulus parameters for the stimulus device based on a combination of the determined first set of responses, the second set of responses, the current sports performance state, the target sports performance state, and the trained artificial intelligence-based system; and the stimulus device is re-configured with the calibrated set of stimulus parameters to apply a new stimulus to the user for a second duration, wherein the use of the new stimulus shifts the current sports performance state towards the target sports performance state.

15. The electronic training system according to claim 14, wherein the control circuitry is further configured to:
determine whether an alteration is required in a training plan for the current sports performance state of the user, based on the application of the new stimulus to the user for the second duration and a shift in at least one sports performance indicator of the user from the current sports performance state towards the target sports performance state;
determine a new training plan that is different from the training plan for the current sports performance state of the user based on the determination that the alteration is required; and
communicate a training change recommendation for the user to a prespecified user device of a coach of the user, wherein the training change recommendation comprises the new training plan for the target sports performance state and a plurality of sports performance indicators that indicates the shift from the current sports performance towards the target sports performance state for the user.

16. The electronic training system according to claim 13, wherein the control circuitry is further configured to:
establish an associative relationship between each stimulus-response pair from the first set of responses and the second set of responses; and
determine a plurality of causes of similarity and variability based on the established associative relationship.

17. A method of electronic evaluation and feedback of sports performance, the method comprising:
in an electronic training system that includes control circuitry:
tracking, by the control circuitry, locomotion and body movements of a user from a set of external response sensors in a first sporting event of a plurality of sporting events;
tracking, by the control circuitry, electrical brain activity and physiological changes in a body of the user from a set of internal response sensors in the first sporting event;
annotating, by the control circuitry, tracked data in the sporting event as a set of period-of-relevance and a set of period-of-irrelevance based on a correlation in the tracked locomotion, the tracked body movements, the tracked electrical brain activity, and the tracked physiological changes for the user in the first sporting event;
assigning, by the control circuitry, a first sports performance state to the user at completion of the sporting event based on a combination of a user feedback and sports statistics acquired from at least one specified data source; and
outputting, by the control circuitry, a first integrated visual motion model on a display device based on annotated tracked data in the set of period-of-relevance, wherein the first integrated visual motion model comprises a first visual representation of the tracked locomotion and the body movements, a second visual representation of the tracked electrical brain activity, and a third visual representation of the tracked physiological changes in the body that are merged in the first integrated visual motion model and time-controlled at output such that the first sports performance state of the user for the first sporting event is discernible by a viewer.

18. The method according to claim 17, further comprising outputting, by the control circuitry, a second integrated visual motion model along the first integrated visual motion model as feedback, based on a comparison of the assigned first sports performance state with a stored learned sports performance dataset that comprises the plurality of historical sports performance states and associated tracked data, and wherein the second integrated visual motion model indicates a set of positive performance activities and a set of negative performance activities in relation to the first sports performance state of the user for the first sporting event or a second sporting event of the plurality of sporting events.

19. The method according to claim 17, further comprising outputting, by a stimulus device of the electronic training system, a first digital environment around the user, wherein the first digital environment is a human-sense stimulating mixed reality environment that induces a specific stimulus to the user to increase sports performance from the first sports performance state to a second sports performance state of the user.

20. The method according to claim 19, further comprising outputting, by the stimulus device, a second digital environment around the user having a second difficulty level that is greater than a first difficulty level of the first digital environment, wherein the second digital environment is a human-sense stimulating mixed reality environment that induces a new stimulus to the user to increase sports performance further from the second sports performance state to a new sports performance state of the user.

* * * * *